United States Patent
Kloke et al.

(10) Patent No.: US 12,409,276 B2
(45) Date of Patent: Sep. 9, 2025

(54) DEAD END CONTAINER AND CONTAINER ASSEMBLY WITH DEAD END CONTAINER

(71) Applicant: SCHOTT PHARMA SCHWEIZ AG, St. Gallen (CH)

(72) Inventors: Arne Kloke, St. Gallen (CH); Anil-Kumar Busimi, St. Gallen (CH); Dominique Bauert, St. Gallen (CH)

(73) Assignee: SCHOTT PHARMA SCHWEIZ AG, St. Gallen (CH)

( * ) Notice: Subject to any disclaimer, the term of this patent is extended or adjusted under 35 U.S.C. 154(b) by 1325 days.

(21) Appl. No.: 17/011,676

(22) Filed: Sep. 3, 2020

(65) Prior Publication Data
US 2021/0060256 A1 Mar. 4, 2021

(30) Foreign Application Priority Data
Sep. 4, 2019 (EP) .................................... 19195405

(51) Int. Cl.
*A61M 5/31* (2006.01)
*A61M 5/315* (2006.01)

(52) U.S. Cl.
CPC ...... *A61M 5/3134* (2013.01); *A61M 5/31513* (2013.01)

(58) Field of Classification Search
CPC .......... A61M 5/31513; A61M 5/31516; A61M 5/3134; A61M 5/3135
See application file for complete search history.

(56) References Cited

U.S. PATENT DOCUMENTS 2,817,458 A * 12/1957 Amigone .............. F25D 31/007
D7/603
5,425,715 A * 6/1995 Dalling ............... A61M 5/2033
604/157
(Continued)

FOREIGN PATENT DOCUMENTS

| GB | 2453432 | 4/2009 |
| WO | 8102572 | 9/1981 |

(Continued)

OTHER PUBLICATIONS

Applied welding Engineering (Third Edition), 2020, 'Chapter 2—Mechanical behaviour of Plastics'. 2020; [Accessed Online Jan. 12, 2025 via Science Direct] https://www.sciencedirect.com/topics/materials-science/stress-concentration?_cf_chl_tk=RuOSTyVIAiFJD1oG3rXhsngF8aGzBghiZUoGw5cx_4A-17367 (Year: 2020).*

(Continued)

*Primary Examiner* — Nathan R Price
*Assistant Examiner* — Mark A Igel
(74) *Attorney, Agent, or Firm* — Ruggiero McAllister & McMahon LLC

(57) ABSTRACT

A container for accommodating pharmaceutical compositions, which is installable in a medical device, is provided. The container includes a hollow cylindrical body having an open end and a dead end opposite to the open end. The dead end is closed by a bottom portion. The hollow cylindrical body and the bottom portion are formed integrally and of the same material. The bottom portion transitions into the hollow cylindrical body via a curved heel that is defined by an outer radius $r_o$, an inner radius $r_i$ and a thickness $d_h$ in a center portion of the curved heel, wherein the following condition is fulfilled: $r_i + d_h - r_o > 0$ mm.

17 Claims, 13 Drawing Sheets

(56) References Cited

U.S. PATENT DOCUMENTS

| | | | | |
|---|---|---|---|---|
| 6,055,829 | A * | 5/2000 | Witzmann | C03B 33/0955 65/56 |
| 2003/0006349 | A1* | 1/2003 | Sadowski | F17C 13/084 248/154 |
| 2006/0173418 | A1* | 8/2006 | Rinaudo | A61M 5/3129 604/230 |
| 2007/0148326 | A1* | 6/2007 | Hastings | A61M 5/31513 604/230 |
| 2008/0245758 | A1* | 10/2008 | Geser | A61M 15/0065 141/2 |
| 2010/0213083 | A1* | 8/2010 | Olander | F17C 11/00 222/6 |
| 2017/0182489 | A1* | 6/2017 | Ebetsberger | A61B 5/154 |
| 2019/0021949 | A1* | 1/2019 | Skufca | A61J 1/006 |

FOREIGN PATENT DOCUMENTS

| | | | |
|---|---|---|---|
| WO | 9119606 | 12/1991 | |
| WO | 2015107953 | 7/2015 | |
| WO | 2018145005 | 8/2018 | |
| WO | WO-2018145005 A1 * | 8/2018 | ........... A01N 1/0263 |

OTHER PUBLICATIONS

ISO 11608-3, "Needle-based injection systems for medical use—Requirements and test methods—Part 3: Finished containers", Second Edition, Oct. 1, 2012, 16 pages.

DIN EN ISO 7458, "Glass containers—Internal pressure resistance—Test methods", May 2004, 8 pages.

DIN EN ISO 8113, "Glass containers—Resistance to vertical load—Test methods", May 2004, 6 pages.

ISO 12775, "Guidelines on types of glass of normal bulk-production composition and their test methods", 1st edition, Oct. 15, 1997, 14 pages.

DIN EN ISO 8362-1, "Injection containers and accessories—Part 1: Injection vials made of glass tubing", Jan. 2020, 16 pages.

DIN ISO 9187-1, "Injection equipment for medical use—Part 1: Ampoules for injectables", Oct. 15, 2010, 16 pages.

* cited by examiner (Prior art)

DEAD END CONTAINER AND CONTAINER ASSEMBLY WITH DEAD END CONTAINER

CROSS REFERENCE TO RELATED APPLICATIONS

This application claims benefit under 35 USC § 119 of European Application 10195405.6, filed Sep. 4, 2019, the entire contents of which are incorporated herein by reference.

BACKGROUND

1. Field of the Invention

The present invention relates to a container for accommodating pharmaceutical compositions, such as compositions of biologics. The container is installable in a medical device, in particular in a medical injector. The invention further relates to a container assembly for accommodating pharmaceuticals and to a medical device for expelling pharmaceuticals.

2. Description of Related Art

Commonly used containers for accommodating pharmaceutical compositions, which are installable in a medical device, are e.g. known from prior art document U.S. Pat. No. 5,425,715 A and are exemplarily shown in FIG. 1. Such prior art container assemblies comprise containers that have a substantially hollow cylindrical body with an open end and an opposite end. The open end is provided for receiving a plunger, while the opposite end has a neck portion with reduced diameter and a flange that is closed by a crimp. For expelling the accommodated pharmaceutical composition by the medical device, the crimp of the container is pierced by a cannula so as to dispense the pharmaceutical therethrough.

However, prior art container assemblies comprising such containers have relatively high space requirements due to the structural configuration of common crimp-type containers.

Another drawback of prior art containers is that some containers tend to break or burst during use, shipping, storage, stoppering and/or filling of the container. In particular, such breaking or bursting can occur if the containers are filled by automated processes in which substantial axial loads are applied to the containers. Moreover, high axial loads that may lead to container damage are applied to the containers when the containers are used in automated sampling machines in scientific labs or medical institutions. Further, breaking or bursting of containers can occur when applying large forces to the container via a plunger, as for example in an epinephrine pen or an emergency drug delivery device.

However, the use of glass containers in pharmaceutical industry only allows a very low failure probability upon application of mechanical stress or pressure changes. To comply with these increased stability requirements, there is a need for improving the strength of glass containers. In order to increase the robustness of containers, the surface of prior art containers can be hardened, for example by means of chemical treatments as disclosed in WO 1981/002572 A1 or in EP 0 495 936 A1. However, such a hardening process requires an additional process step in the manufacturing of containers and—in case of chemical treatments—also leads to a modification of the surface. Therefore, a chemically strengthened glass surface typically requires a new market authorization of the glass container.

SUMMARY

It is an object of the present invention to provide a container for accommodating pharmaceutical compositions and being installable in a medical device, a corresponding container assembly, and a medical device for expelling pharmaceutical compositions, which overcome the above drawbacks.

In particular, it is an object of the present invention to provide a container for accommodating pharmaceutical compositions and being installable in a medical device, a corresponding container assembly, and a medical device for expelling pharmaceutical compositions, which have an increased resistance against mechanical stress and/or pressure changes.

It is a further object of the present invention to provide a container for accommodating pharmaceutical compositions and being installable in a medical device, and a corresponding container assembly, which allow for a compact design of the medical device, and to provide a medical device for expelling pharmaceutical compositions, which has a compact size and geometry.

These objects are achieved by the subject matter disclosed herein.

According to a first aspect, the present invention provides a container for accommodating pharmaceutical compositions, in particular biologics. In this description, the term "pharmaceutical composition" refers to a composition that comprises at least a pharmaceutically active agent, and at least one pharmaceutically acceptable excipient, such as a carrier. The pharmaceutically active agent may be a so-called "biological", or "biologic". Biologicals/biologics include proteins, peptides, nucleic acids, vaccines, antibodies, and enzymes. Preferably, the container is suitable for accommodating parenterals in accordance with section 3.2.1 of the European Pharmacopoeia, 7th edition from 2011.

The container is installable in a medical device, in particular in a medical injector, a medical injection pen or an emergency drug delivery device. The container can also be referred to as a cartridge, an expelling or injection container or an injection cartridge. The container can be installable in a container assembly which can be installable in a medical device. The medical device can be a medical injector or medical injection pen, such as an injector for injecting epinephrine (i.e. an epinephrine pen). The medical device can be automatically and/or manually operable. The medical device can be fluidically connected to a dispensing arrangement, such as to a tube of an injection or dispensing arrangement.

The container comprises a hollow cylindrical body having an open end and a dead or closed end (herein after dead end) opposite to the open end. The open end completes or borders the container on one side of the container. The open end comprises a front surface. The front surface forms a circular ring.

The hollow cylindrical body can have a wall thickness $d_w$. The wall thickness can define the width of the front surface. Preferably, the hollow cylindrical body has a length L between 35 mm and 120 mm, more preferably between 42 and 70 mm. Preferably, the hollow cylindrical body has an outer diameter $D_o$ between 8.65 mm and 30 mm, more preferably between 8.65 mm and 22.05 mm. Preferably, the hollow cylindrical body has an inner diameter $D_I$ between 4.65 mm and 27 mm, more preferably between 6.85 mm and 19.05 mm. Preferably, the hollow cylindrical body has a length to outer diameter ratio $L/D_o$ between 3:1 and 15:1, more preferably between 3:1 and 12:1, more preferably between 3:1 and 10:1, more preferably between 3:1 and 7:1, more preferably between 4:1 and 7:1, more preferably between 5:1 and 7:1 and more preferably between 6:1 and 7:1.

Preferably, the outer diameter $D_o$ and/or the inner diameter $D_I$ of the hollow cylindrical body does not vary more than 5% over the entire length L of the hollow cylindrical body, respectively, more preferably not more than 4%, preferably not more than 3%, more preferably not more than 2%, even more preferably not more than 1%. With other words, the outer diameter $D_o$ and/or the inner diameter $D_I$ is substantially constant over the entire length L of the hollow cylindrical body. This means that the container does not comprise any neck portion or the like in an end region of the container as known from prior art containers and cartridges.

The open end of the container is configured for receiving a plunger that is slidable relative to the hollow cylindrical body from the open end towards the dead end. The dead end is closed by a bottom portion, wherein the hollow cylindrical body and the bottom portion are formed integrally and of the same material, which is a glass or polymer material. Thus, the completely closed dead end of the container is not pierceable by a cannula. Consequently, in a medical device or a container assembly comprising the dead end container, both the plunger actuation for acting upon the accommodated pharmaceutical compositions and the fluidic connection for dispensing the pharmaceutical compositions by a cannula have to be realized via the open end (e.g. by penetrating the plunger with the cannula).

The bottom portion transitions or merges into the hollow cylindrical body via a curved heel that is defined by an outer radius $r_o$, an inner radius $r_i$ and a thickness $d_h$ in a center portion of the curved heel. The container has a structural configuration, wherein the following condition is fulfilled: $r_i+d_h-r_o>0$ mm, preferably $r_i+d_h-r_o>0.1$ mm, more preferably $r_i+d_h-r_o>0.25$ mm, even more preferably $r_i+d_h-r_o>0.5$ mm and still more preferably $r_i+d_h-r_o>0.75$ mm.

Providing a container with the specified structural configuration, including implementing the specified shapes and dimensions and fulfilling the above condition, improves the mechanical properties of the container and especially reduces the fracture risk by providing an advantageous relationship between weak points due to hot formed bottom parts, container dimensions and material accumulation in certain container regions. In particular, the resistance of the container against mechanical stress and/or pressure changes can be increased compared to prior art containers.

Moreover, providing the container with one dead end allows for a desired inner volume capacity while reducing the length of the container, and thus of a corresponding container assembly, compared to prior art containers with a neck portion and a crimp. By means of the dead end, the neck portion and the crimp (including a sealing rubber member) can be omitted, which can result in an overall length reduction of more than 5 mm with regard to containers having an inner volume capacity of 1 ml, 1.5 ml or 3 ml and an even greater length reduction with regard to containers having an inner volume capacity of 5 ml or more. Therefore, the dead end structure of the container and the specific length and diameter values and ratios of the container lead to a compact overall design of the container, which consequently allows for a compact design of a corresponding medical device. Further, by omitting the neck portion, the crimp and the sealing rubber member, the number of separate components and materials of the container can be reduced, which reduces manufacturing costs of the container.

In a preferred embodiment, the container has a particular structural configuration, wherein in the following formula:

$$D \times Ts \pm L = A,$$

in which L is the length of the hollow cylindrical body in mm, D is the difference of the outer diameter $D_o$ of the hollow cylindrical body minus the inner diameter $D_I$ of the hollow cylindrical body in mm, and Ts is the tensile strength of the material in MPa, the following condition is fulfilled: MPa≤A≤12.00 MPa, preferably 1.50 MPa≤A≤8.00 MPa, more preferably 2.00 MPa≤A≤7.00 MPa, even more preferably 3.00 MPa≤A≤6.00 MPa, still more preferably 3.50 MPa≤A≤4.50 MPa.

In a preferred embodiment, the container has a particular structural configuration, wherein in the following formula:

$$D \times E \pm L = B,$$

in which L is the length of the hollow cylindrical body in mm, D is the difference of the outer diameter $D_o$ of the hollow cylindrical body minus the inner diameter $D_I$ of the hollow cylindrical body in mm, and E is the Young's modulus of the material in GPa, the following condition is fulfilled: 0.10 GPa.≤B≤10.00 GPa, preferably 1.00 GPa≤B≤7.50 GPa, more preferably 2.00 GPa≤B≤7.00 GPa, even more preferably 3.00 GPa≤B≤6.00 GPa, still more preferably 4.00 GPa≤B≤5.00 GPa.

A preferred embodiment of the container fulfilling one or more of the preferred conditions provides an advantageous structural configuration, which further improves the mechanical properties of the container. In particular, fulfillment of one or both of the above conditions provides a structural container configuration that reduces the fracture risk by providing a preferable relationship between weak points due to hot formed bottom parts, container dimensions and material properties (tensile strength and/or Young's modulus). In addition, by fulfilling one or more of the preferred conditions it can be secured that the container containing a liquid pharmaceutical composition can be emptied without any liquid leaking through a gap between the plunger and the side wall of the container, in particular when applying large forces to the container via a plunger.

The container preferably has a pressure compliance F (force) of at least 0.64 N/mm²×(inner diameter)², i.e. of at least 0.64 N/mm²×inner diameter×inner diameter. More preferably, the container can have a pressure compliance F (force) of at least 0.75 N/mm²×(inner diameter)², more preferably at least 0.8 N/mm²×(inner diameter)², more preferably at least 0.85 N/mm²×(inner diameter)², more preferably at least 0.9 N/mm²×(inner diameter)², and still more preferably at least 0.95 N/mm²×(inner diameter)². The pressure compliance constitutes a minimal axial force that is applyable to the filled container via the plunger, without any leakage occurring on the container assembly. Measurement of the pressure compliance can be performed in accordance with the settings set forth in ISO 11608-3:2012. Such a pressure compliance reduces the risk of damaging the container during use in a medical device, in particular when applying large forces to the container via a plunger, as for example in an epinephrine pen or an emergency drug delivery device. The improved shape and dimensions of the dead-end container contributes to providing the container assembly with the preferred pressure compliance. This applies in particular as the inventors have observed that the leakage mainly occurs at the crimped closure of prior art container assemblies (and not in the region of the plunger). Thus, by replacing the crimped closure with an integral dead end, this weak point can be avoided.

A container according to the invention preferably exhibits an improved burst pressure. The burst pressure or burst strength describes the internal pressure that the hollow cylindrical container can handle before rupturing or bursting. The preferred burst pressure reduces the risk of damaging the container both during transportation or storage and during use of the container (assembly). The mechanical resistance against internal pressure of the container can be determined by means of burst strength testing in accordance to DIN EN ISO 7458:2004-05 ("Glass containers—Internal pressure resistance—Test methods"), where a hydraulic pressure is applied from inside of the container and is increased with a constant load rate of 5.8 bar/s until breakage of the container. In a preferred embodiment, the container has a burst pressure of at least 110%, more preferably at least 120%, even more preferably at least 130% compared to a container which only differs in that the container does not fulfil the requirement $r_i + d_h - r_o > 0$ mm.

A container according to the invention exhibits an improved vertical load strength. The vertical load strength describes the mechanical resistance against axial compression of the container. This resistance can be determined by means of vertical load strength testing in accordance to DIN EN ISO 8113:2004-05 ("Glass containers—Resistance to vertical load—Test methods"), where a compressive force is applied in axial direction and is increased with a constant load rate of 500 N/min until breakage of the container. In a preferred embodiment, the container has a vertical load strength of at least 110%, more preferably at least 120%, even more preferably at least 130% compared to a container which only differs in that the container does not fulfil the requirement $r_i + d_h - r_o > 0$ mm.

In a preferred embodiment of the container, the dead end is defined by the wall thickness $d_w$ of the hollow cylindrical body, the outer radius $r_o$ of the curved heel, the inner radius $r_i$ of the curved heel and the thickness in the center portion of the curved heel.

The following condition can be fulfilled: $d_h^3 \pm (r_o \times d_w) > 0.8$ mm, preferably $d_h^3 \pm (r_o \times d_w) > 1.0$ mm, more preferably $d_h^3 \pm (r_o \times d_w) > 1.2$ mm, even more preferably $d_h^3 \pm (r_o \times d_w) > 1.5$ mm, and still more preferably $d_h^3 \pm (r_o \times d_w) > 2.0$ mm, wherein $d_h$ is the thickness in the center portion of the curved heel, $r_o$ is the outer radius of the curved heel, and $d_w$ is the wall thickness of the hollow cylindrical body.

In particular, the following condition can be fulfilled: $d_h^3 \pm (r_o \times d_w) \leq 7.0$ mm, preferably $d_h^3 \pm (r_o \times d_w) < 5.0$ mm, and more preferably $d_h^3 \pm (r_o \times d_w) < 4.0$ mm.

In a preferred embodiment of the container, the following condition is fulfilled: $[100 \times (d_h^3 \times r_i) \pm (d_w \times D_o^2)] + (4.4 \text{ mm}^2 \pm D_o) > 0.55$ mm, preferably $[100 \times (d_h^3 \times r_i) \pm (d_w \times D_o^2)] + (4.4 \text{ mm}^2 \pm D_o) > 0.75$ mm, more preferably $[100 \times (d_h^3 \times r_i) \pm (d_w \times D_o^2)] + (4.4 \text{ mm}^2 \pm D_o) > 1.00$ mm, even more preferably $[100 \times (d_h^3 \times r_i) \pm (d_w \times D_o^2)] + (4.4 \text{ mm}^2 \pm D_o) > 1.50$ mm, and still more preferably $[100 \times (d_h^3 \times r_i) \pm (d_w \times D_o^2)] + (4.4 \text{ mm}^2 \pm D_o) > 2.00$ mm, wherein $d_h$ is the thickness in the center portion of the curved heel, $r_i$ is the inner radius of the curved heel, $d_w$ is the wall thickness of the hollow cylindrical body, and $D_o$ is the outer diameter of the hollow cylindrical body.

In particular, the following condition can be fulfilled: $[100 \times (d_h^3 \times r_i) \pm (d_w \times D_o^2)] + (4.4 \text{ mm}^2 \pm D_o) < 20$ mm, preferably $[100 \times (d_h^3 \times r_i) \pm (d_w \times D_o^2)] + (4.4 \text{ mm}^2 \pm D_o) < 10$ mm, and more preferably $[100 \times (d_h^3 \times r_i) \pm (d_w \times D_o^2)] + (4.4 \text{ mm}^2 \pm D_o) < 5$ mm.

According to a preferred embodiment, the following condition is fulfilled: $r_i > 0.7$ mm, preferably $r_i > 0.8$ mm, more preferably $r_i > 0.9$ mm, even more preferably $r_i > 1.0$ mm, and still more preferably $r_i > 1.2$ mm, wherein $r_i$ is the inner radius of the curved heel.

In a preferred embodiment, the inner radius $r_i$ of the curved heel is in the range from 0.6 mm to 4.0 mm, preferably in the range from 0.7 mm to 3.0 mm, more preferably in the range from 0.8 mm to 2.5 mm, even more preferably in the range from 0.85 mm to 2.0 mm and still more preferably in the range from 0.9 mm to 1.6 mm.

In a preferred embodiment, the wall thickness $d_w$ of the container is in the range from 0.5 mm to 3.0 mm, preferably in the range from 0.7 mm to 1.8 mm, more preferably in the range from 0.8 mm to 1.2 mm, even more preferably in the range from 0.9 mm to 1.1 mm and still more preferably in the range from 0.95 mm to 1.05 mm.

In a preferred embodiment, the thickness $d_h$ in the center portion of the curved heel is in the range from 1.0 mm to 5.0 mm, preferably in the range from 1.05 mm to 3.0 mm, more preferably in the range from 1.15 mm to 2.5 mm, even more preferably in the range from 1.3 mm to 2.0 mm and still more preferably in the range from 1.4 mm to 1.9 mm.

In a preferred embodiment, the outer radius $r_o$ of the curved heel is in the range from 0.5 mm to 4.0 mm, preferably in the range from 1.1 mm to 3.0 mm, more preferably in the range from 1.2 mm to 2.5 mm, even more preferably in the range from 1.3 mm to 2.0 mm and still more preferably in the range from 1.4 mm to 1.7 mm.

In a preferred embodiment, the outer diameter $D_o$ of the hollow cylindrical body is in the range from 15 mm to 30 mm, preferably in the range from 15 mm to 20 mm.

In a preferred embodiment, the inner diameter $D_I$ of the hollow cylindrical body is in the range from 12 mm to 25 mm, preferably in the range from 12 mm to 17 mm.

In a preferred embodiment, the container has a structural configuration, in which the following condition is fulfilled: $r_o < 3.0 \times d_w$, preferably $r_o < 2.0 \times d_w$, more preferably $r_o < 1.5 \times d_w$, in particular $r_o < 1.4 \times d_w$, preferably $r_o < 1.3 \times d_w$, more preferably $r_o < 1.2 \times d_w$, even more preferably $r_o < 1.0 \times d_w$ and still more preferably $r_o < 0.8 \times d_w$, wherein $r_o$ is the outer radius of the curved heel and $d_w$ is the wall thickness of the hollow cylindrical body.

In a preferred embodiment, the container has a structural configuration, in which the following condition is fulfilled: $d_h > 1.05 \times d_w$, preferably $d_h > 1.15 \times d_w$, more preferably $d_h > 1.25 \times d_w$, even more preferably $d_h > 1.4 \times d_w$ and still more preferably $d_h > 1.6 \times d_w$, wherein $d_h$ is the thickness in the center portion of the curved heel and $d_w$ is the wall thickness of the hollow cylindrical body.

In a preferred embodiment, the container has a thickness $d_{cgb}$ at the center of the bottom portion forming the dead end, wherein the following condition is fulfilled: $d_h - d_{cgb} > 0.5$ mm, preferably $d_h - d_{cgb} > 1.0$ mm, more preferably $d_h - d_{cgb} > 1.5$ mm, even more preferably $d_h - d_{cgb} > 2.0$ mm and still more preferably $d_h - d_{cgb} > 3.0$ mm, wherein $d_{cgb}$ is the thickness at the center of the bottom portion and $d_h$ is the thickness in the center portion of the curved heel.

In a preferred embodiment, the thickness $d_{cgb}$ at the center of the bottom portion is in the range from 0.6 mm to 2.5 mm, preferably in the range from 1.0 mm to 2.0 mm, more preferably in the range from 1.05 mm to 1.7 mm, even more preferably in the range from 1.1 mm to 1.6 mm and still more preferably in the range from 1.2 mm to 1.5 mm.

In a preferred embodiment, the bottom portion has a circular shape. This circular bottom can have a thickness that varies within an area from the center of the circular bottom to an outer area of the circular bottom. In particular, the following condition can be fulfilled: $d_h \pm d_{b,min} < 3.0$, preferably $d_h \pm d_{b,min} < 2.5$, more preferably $d_h \pm d_{b,min} < 2.0$, even more preferably $d_h \pm d_{b,min} < 1.6$, and still more preferably $d_h \pm d_{b,min} < 1.2$, wherein $d_h$ is the thickness in the center portion of the curved heel and $d_{b,min}$ is the minimum thickness of the circular bottom.

Preferably, $d_{b,min}$ is in the range from 0.6 mm to 3.0 mm, preferably in the range from 0.8 mm to 2.5 mm, more preferably in the range from 1.0 mm to 2.0 mm, even more preferably in the range from 1.2 mm to 1.8 mm and still more preferably in the range from 1.4 mm to 1.7 mm.

In a preferred embodiment, a contour of the cross section of the circular bottom on a side directed towards the interior side of the container is characterized by not more than two inflection points over the whole diameter of the circular bottom.

In a preferred embodiment, the circular bottom is characterized by a bottom diameter $D_{bottom}$, wherein $D_{bottom} = D_O - 2 \times r_o$, wherein $D_O$ corresponds to the outer diameter of the hollow cylindrical body and wherein $D_{bottom}$ is in the range from 10 mm to 50 mm, preferable in the range from 12 mm to 30 mm and more preferably in the range from 13 mm to 25 mm.

In a preferred embodiment, the curved heel has an outer surface having the form of a circular arc, wherein in particular the circular arc has a length $l_o$ of $2 \times \pi \times r_o / 4$ or in the range from $(50°/360°) \times 2\pi \times r_o$ to $(80°/360°) \times 2\pi \times r_o$, or preferably in the range from $(60°/360°) \times 2\pi \times r_o$ to $(80°/360°) \times 2\pi \times r_o$.

According to a preferred embodiment, throughout the entire region of the hollow cylindrical body the wall thickness $d_w$ of the container is in a range from ±0.2 mm, preferably ±0.1 mm, more preferably ±0.08 mm and even more preferably ±0.05 mm, in each case based on a nominal value of this wall thickness in the body region.

In a preferred embodiment, the container has a mass of glass $m_g$ and an interior volume $V_i$, wherein the following condition is fulfilled: $m_g / V_i^{0.75} < 2.0$, preferably $m_g / V_i^{0.75} < 1.75$.

In a preferred embodiment, the container has an interior volume $V_i$ in a range from 2 to 150 ml, preferably from 3 to 100 ml, more preferably from 3 to 50 ml, even more preferably from 3 to 15 ml, still more preferably from 3 to 7 ml.

As used herein, the interior volume $V_i$ represents the full volume of the interior of the container. This volume may be determined by filling the interior of the container with water up to the brim and measuring the volume of the amount of water which the interior can take up to the brim. Hence, the interior volume as used herein is not a nominal volume as it is often referred to in the technical field of pharmacy. This nominal volume may for example be less than the interior volume.

According to an embodiment, the container can be a glass container. As the portions of the container are formed integrally, i.e. in a one-piece form, and of the same material, it means that in this embodiment the hollow cylindrical body and the bottom portion forming the dead end and comprising the curved heel are glass components. In particular, the container material can be a borosilicate glass, an aluminosilicate glass, a soda lime glass or a fused silica. "Soda lime glass" according to the invention is an alkaline/alkaline earth/silicate glass according to table 1 of ISO 12775 (1st edition 1997-10-15).

Preferred materials have the following compositional ranges in mol %:

| component | mol % |
| --- | --- |
| $SiO_2$ | 60 to 85 |
| $B_2O_3$ | 3 to 15 |
| $Al_2O_3$ | 0 to 5 |
| $R_2O$ | 5 to 15 |
| RO | 0 to 10 | wherein $R_2O$ means the alkali metal oxides selected from $Li_2O$, $Na_2O$ and $K_2O$; and RO means the metal oxides selected from MgO, ZnO, CaO, BaO and SrO.

Preferably, the material has an average linear thermal coefficient of expansion a (20° C., 300° C.) of 3 to $11 \cdot 10^{-6}/K$, preferably 3.5 to $7 \cdot 10^{-6}/K$, more preferably about $4.9 \cdot 10^{-6}/K$. The material can have a transformation temperature Tg of 400° C. to 700° C., preferably about 565° C. The material can have can have a density $\varrho$ at 25° C. of 2.3 to 2.5 grams (g) per cubic centimeter ($cm^3$), preferably about 2.34 grams (g) per cubic centimeter ($cm^3$).

The glass container can be thermally tempered, chemically tempered or both.

In a preferred embodiment, the container is a tubular glass container prepared from prefabricated glass tubing by shaping and separation.

According to an embodiment, the container can be a polymer container. As the portions of the container are formed integrally and of the same material, it means that in this embodiment the hollow cylindrical body and the bottom portion forming the dead end and comprising the curved heel are polymer components. In particular, the container material can be a cycloolefin copolymer or a cycloolefin polymer.

In a preferred embodiment, the inner surface of the container has an average Zn-leachability (zinc leachability) of 0.00085 µg/cm² or less, preferably 0.00075 µg/mm² or less, more preferably 0.00065 µg/mm² or less, still more preferably 0.00055 µg/mm² or less. The leachability values relate to measurement results from an ICP-MS (inductively coupled plasma mass spectrometry) analysis method. An optional and preferred way of measuring the leachabilities indicated in this description is given in the example section.

This preferable configuration effectively increases the shelf-life of pharmaceutical compositions accommodated in a container. The inventors of the present invention have identified the presence and negative effects of Zn-leachables in prior art containers and container assemblies and have determined that minimizing especially the Zn-leachability to the specified amounts leads to an increased shelf-life of pharmaceuticals stored in the container. Hence, this embodiment provides an advantageous solution for a container that is installable in a medical device and minimizes the Zn-leachability, i.e. increase the shelf-life of pharmaceuticals, by means of a particular feature combination. This feature combination includes an optimized shape and dimensions of the container as well as specific material parameters. Optimal shape and dimensions are achieved by providing the container with a dead end, which allows for a compact size and the specified length and diameter values and ratios, which constitute an optimal balance between favorable inner surface-to-volume ratio and a favorable inner diameter, considering that in a container assembly the inner diameter of the container influences the surface of the rubber plunger in contact with the accommodated pharmaceutical composition. Both the inner surface of the container and the surface of the rubber plunger, which may be in contact with an accommodated pharmaceutical during storage, influence the amount of leachables, such as Zn-leachables, migrating into the accommodated pharmaceutical. Further, the average Zn-leachability of the container material influences the amount of leachables, such as Zn-leachables, migrating into the accommodated pharmaceutical. Hence, the feature combination of the container of this preferred embodiment, including the optimized shape and dimensions and the specific material parameters of the container synergistically contributes to an increase the shelf-life of pharmaceuticals accommodated in the container.

It was further found that leachability values can be influenced by the cooling rate used during production of the glass material, e.g. after drawing a glass tube for forming the container. It was found that if the glass undergoes very fast cooling, diffusivity increases whereas hydrolytic, acid resistance and leaching increases. Diffusivity is the susceptibility of the material towards chemical tempering. If the glass cools very slowly, diffusivity decreases, hydrolytic as well as acid resistance increase and leaching is reduced. The effective cooling result can be measured on a given glass article simply by measuring the compaction that a glass article undergoes under controlled temperature conditions, wherein higher compaction corresponds to fast cooling and lower compaction corresponds to slow cooling. Particularly, it was found that desired diffusivity, leaching characteristics, hydrolytic and/or acid resistance values can be obtained, if the glass material used in this invention is produced such that the glass exhibits a compaction of from 50 to 120 µm per 100 mm length. Preferably, compaction should be in a range of from 60 to 100 µm, or from 65 to 95 µm per 100 mm length.

Such a compaction can be particularly helpful for minimizing Zn-leachability (and other leachability in general, e.g. of Mg, Al), in particular in order to provide an average Zn-leachability of the inner surface of the container of 0.00135 µg/cm$^2$ or less, preferably 0.00115 µg/mm$^2$ or less, more preferably 0.00100 µg/mm$^2$ or less, still more preferably 0.00080 µg/mm$^2$ or less. Preferably, the material having this compaction can be a glass material.

Compaction measurement is very simple. An article or part of an article (made of the material) of a given length, e.g. a tube or container, or a part thereof, is subjected to heat, wherein the article or part thereof is heated from room temperature to 500° C. by putting the article or part thereof into an oven (pre-heated to 500° C.), kept in the oven at 500° C. for 1 hour, and cooled back to room temperature by taking the article or part thereof out of the oven and letting it cool down at room temperature in ambient atmosphere. Room temperature is 20° C. The length of the article or part thereof is measured before and after heat treatment. The length is the article's diameter or the diameter of its part along its respective longitudinal axis.

According to another aspect, the present invention provides a container assembly for accommodating pharmaceutical compositions. The container assembly is installable in a medical device and comprises a container of the type described above, and a plunger that is arranged inside the hollow cylindrical body in the region of the open end so as to sealingly close the open end. The plunger is pierceable by a cannula and is slidable relative to the hollow cylindrical body from the open end towards the dead end.

In a preferred embodiment of the container assembly, the plunger comprises a rubber material having a Zn-leachability of 0.00800 µg/cm$^2$ or less, preferably 0.00650 µg/cm$^2$ or less, more preferably 0.00500 µg/cm$^2$ or less, still more preferably 0.00350 µg/cm$^2$ or less. Providing the plunger with a respective rubber material can further increased shelf-life of pharmaceuticals stored in the container by further minimizing the overall amount of Zn migrating into the accommodated pharmaceutical, considering that an inner surface of the plunger is in contact with the accommodated pharmaceutical during storage and use of the container assembly.

The plunger can be entirely or partially be made of the rubber material. In an embodiment, in which the plunger is only partially made of rubber material, the rubber can for example comprise a substantially cylindrical non-rubber component (e.g. thermoplastic, ceramic, glass) with a rubber O-ring, e.g. arranged on a lateral surface of the cylindrical non-rubber component. The substantially cylindrical non-rubber component can comprise the same material as the container or a different material than the container.

Preferably, the plunger comprises, or essentially consist of, an elastomeric material, such as a rubber. Generally, the elastomeric material may be any suitable elastomer, and more particularly, rubbers constructed from butyl, bromobutyl, chlorobutyl, silicone, nitrile, styrene butadiene, polychloroprene, ethylene propylene diene, fluoroelastomers, thermoplastic elastomers (TPE), and combinations and blends thereof.

In a preferred embodiment, the inner surface of the container assembly has an average Zn-leachability of 0.00135 µg/cm$^2$ or less, preferably 0.00115 µg/mm$^2$ or less, more preferably 0.00100 µg/mm$^2$ or less, still more preferably 0.00080 µg/mm$^2$ or less. The inner surface of the container assembly comprises the inner surface of the container, i.e. the inner surface of the hollow cylindrical body and of the bottom portion, and the inner surface of the plunger. Thus, providing a material combination that has the specified Zn-leachability can particularly increase shelf-life of pharmaceuticals stored in the container assembly.

In a preferred embodiment, the inner surface of the container assembly has an average Mg-leachability (magnesium leachability) of 0.04000 µg/cm$^2$ or less, preferably 0.03700 µg/cm$^2$ or less, more preferably 0.03500 µg/cm$^2$ or less, still more preferably 0.03200 µg/cm$^2$ or less. The inventors of the present invention have further identified the presence and negative effects of Mg-leachables in prior art container assemblies and have determined that minimizing also the Mg-leachability to the specified amounts leads to a further increased shelf-life of pharmaceutical compositions accommodated in the container assembly.

According to another aspect, the present invention provides a medical device for expelling or injecting pharmaceutical compositions. The medical device comprises a hollow device body, a container assembly of the type described above, and a cannula for expelling the pharmaceutical compositions from the container assembly through the cannula. The cannula is arranged so as to pierce the plunger upon actuation of the medical device. The medical device further comprises an actuation mechanism which is configured to move the container and the plunger relative to each other in a substantially axial direction inside the hollow device body so as to apply pressure to the pharmaceutical compositions accommodated in the container for expelling the pharmaceutical compositions.

The medical device can further comprise a trigger that is manually operable, wherein the trigger upon operation causes actuation of the actuation mechanism, e.g. by mechanically releasing a retaining or locking mechanism.

The medical device can comprise a pharmaceutical composition accommodated in the container.

Compared to common medical devices, the medical device according to the invention has a more compact size and design by means of the container assembly comprising the compact dead end container.

Even though some of the features, functions, embodiments, technical effects and advantages have been described with regard to the container, the container assembly or the medical device, it will be understood that these features, functions, embodiments, technical effects and advantages can also apply accordingly to the container, the container assembly and/or the medical device. Particularly, all preferred embodiments for the container apply also for the container assembly and the medical device and the other way around unless specified otherwise.

Measurement Methods

The following measurement methods can be used in the context of the invention. Unless otherwise specified, the measurements have to be carried out at an ambient temperature of 23° C., an ambient air pressure of 100 kPa (0.986 atm) and a relative atmospheric humidity of 50%.

Determination f $r_i$, $r_o$ And $D_h$

The inner diameter $r_i$, the outer diameter $r_o$ and the thickness $d_h$ of the curved heel can be determined in an non-destructive manner using a profile projector. This approach is particularly suitable for glass containers that have been chemically and/or thermally tempered and that therefore cannot be easily sliced in half without the glass cracking or bursting. For determining $r_i$, $r_o$ and $d_h$ in a non-destructive manner radius templates are used that are commercially available, for example, from Mitutoyo Deutschland GmbH, Neuss, Germany. These templates are printed on a transparent foil which, after applying a line that indicates the ground-level bearing surface and a tangent that confines an angle of 45° with the ground-level bearing surface, is glued to the ground glass of a Mitutoyo PJ-3000 profile projector. The profile projector has a 10× magnification and is operated with transmitted light illumination. The vials are placed in Hallbrite® BHB (a butyloctyl salicylate obtainable from the Hallstar Company, Chicago, USA), which is filled into a glass bowl. Hallbrite® BHB is used to visualize the inner contour of the vial. It is ensured that the cross-section of the container that is inspected in the profile projector corresponds to the plane that is centrically located in the container and that comprises the longitudinal axis of the container, i. e. the axis that goes perpendicular through the centre of the bottom (see FIGS. 7A and 7B).

To improve the measuring accuracy, $r_i$, $r_o$ and $d_h$ can also be determined from a physical cross-sectional cut parallel along to the longitudinal axis of the container (it is again ensured that the cross-section of the container corresponds to the plane that is centrically located in the container and that comprises the longitudinal axis as shown in FIGS. 7A and 7B). For preparation without breakage, the container may be embedded into transparent 2-component epoxy resin, for example STRUERS GmbH, EpoFix Resin or other suitable materials. After curing of the epoxy resin, a cross-sectional cut parallel along to the container axis can be achieved by machine-supported sawing, grinding and polishing. Geometrical features of the container can then be determined (measured) by means of non-distorting image capturing and geometrical analysis software tools.

In the cross-sectional plane of the container that is evaluated by means of the two approaches described above $r_i$, $r_o$ and $d_h$ can be determined as follows, preferably is determined as follows:

For the determination of $d_h$ a tangent that confines an angle of 45° with the ground-level bearing surface (i.e. the surface that comes into contact with the exterior side of the container bottom if the container is placed upright) is placed at the exterior surface of the curved heel as shown in FIG. 8A (the dashed line indicates the 45°-tangent). The point of the exterior surface of the curved heel that comes into contact with the 45°-tangent is designated as "A" (see FIG. 8A). Next, a straight line orthogonal to 45°-tangent is guided through point "A" (the dotted line in FIG. 8A indicates the orthogonal line). The position at which this straight orthogonal line breaks through the interior side of the curved heel is designated as "B" (see FIG. 8A). $d_h$ corresponds to the distance between points "A" and "B".

If there are more than only one point of exterior surface of the curved heel that comes into contact with the 45°-tangent (as shown, for example, in FIG. 8B), point "A" corresponds to the point that is nearest to the outer surface of the hollow cylindrical body. However, according to a particular embodiment of the container according to the invention the curved heel has a shape such that, when placing the 45°-tangent to the exterior surface of the curved heel, there is only one point of exterior surface of the curved heel that comes into contact with the 45°-tangent.

For the determination of $r_o$ the intersection point of a first straight line that forms an elongation of the exterior side of the hollow cylindrical body and the ground-level bearing surface is determined (see the vertical dashed line in FIG. 9A). If the curved heel laterally extends over the first straight line that forms an elongation of the exterior side, the first line goes through the curved heel until it reaches the ground-level bearing surface. The intersection point is designated as "C". Next, the point of the exterior surface of the container that contacts the ground-level bearing surface and that is closest to point "C" is determined. This intersection point is designated as "D" (see FIG. 9A). $r_o$ corresponds to the distance between points "C" and "D". In case of a curved heel having a circular arc $l_o$ at the outer surface of the curved heel with a length of $2\times\pi\times r_o/4$ (see, for example, the shape of the curved heel in FIG. 2), the distance between points "C" and "D" corresponds to the radius $r_o$ of the circle that is defined by the shape of the outer surface of the curved heel. However, the container according to the present invention is not limited to containers in which the circular arc $l_o$ at the outer surface of the curved heel has a length of $(90°/360°)\times 2\times r_o$, but also comprises containers in which this circular arc $l_o$ is smaller (see, for example, the shape of the curved glass heel in FIG. 6 in which the outer area of the bottom somehow "extends" into the area of the curved heel) or containers in which the outer surface of the curved heel is not shaped in the form of a circular arc at all. In these cases $r_o$ actually does not correspond to the outer radius of the curved heel, but to width of the material overhang in the area of the curved heel that is defined by the distance between points "C" and "D".

For the determination of $r_i$ a tangent that confines an angle of 45° with the ground-level bearing surface is placed at the interior surface of the curved heel as shown in FIG. 8B (the dashed line indicates the 45°-tangent). The point of the interior surface of the curved heel that comes into contact with the 45-tangent is designated as "E" (see FIG. 9B). Next, the largest quarter circle is determined that can be properly positioned on the inner contour of the curved heel, that comprises point "E" in the middle of the quarter circle and the ends of which do not extending into the mass of material. $r_i$ corresponds to the radius of the largest quarter circles.

If there are more than only one point of interior surface of the curved heel that comes into contact with the 45°-tangent, point "E" corresponds to the geometric centre between points "P1" and "P2", wherein point "P1" is the point on the 45°-tangent that comes into contact with the interior surface of the curved heel and that is located nearest to the hollow cylindrical body and point "P2" is the point on the 45°-tangent that comes into contact with the interior surface of the curved heel and that is located nearest to the bottom. However, according to a particular embodiment of the container according to the invention the curved heel has a shape such that, when placing the 45°-tangent to the interior surface of the curved heel, there is only one point of interior surface of the curved heel that comes into contact with the 45-tangent.

Wall Thickness $d_w$ And Tolerance Of Wall Thickness

The wall thickness and deviations from the mean value of the wall thickness (tolerance) can be determined in accordance with the following standards: DIN ISO 8362-1:2015-10 or DIN ISO 9187-1:2010-10.

Leachability

All of the leachability values mentioned herein can relate to measurement results from an ICP-MS (inductively coupled plasma mass spectrometry) analysis method, in particular as specified below. The leachability values, i.e. a leachability of X µg/cm² or less, means that the respective surface or material releases X µg or less of the respective leachable per cm².

For analyzing the average leachability by means of ICP-MS, portions of test and control extracts can be prepared in suitable plastic containers and can be acidified to approximately 2% with concentrated nitric acid. The resulting solutions can be analyzed with the following method and instrumental parameters:

TABLE 1

| ICP-MS; INSTRUMENTAL PARAMETERS | |
| --- | --- |
| Timing Parameters | |
| Sweeps/Readings | 20 |
| Readings/Replicate | 1 |
| Number of Replicates | 3 |
| Signal Processing | |
| Detector Mode | Dual |
| AutoLens | On |
| Spectral Peak Processing | Average |
| Signal Peak Processing | Average |
| Blank Subtraction after internal standard | |
| Pump Parameters | |
| Sample Analysis Speed | 24 mL/min |
| Sample Flush Time | 80-120 sec |
| Sample Flush Speed | 48 mL/min |
| Read Delay Time | 30-45 sec |

TABLE 2

| ICP-MS; ION MASS USED FOR ANALYSIS | |
| --- | --- |
| Element | Mass |
| Mg | 24 |
| Al | 27 |
| Zn | 66 |

BRIEF DESCRIPTION OF THE DRAWINGS

For a better understanding of embodiments of the invention and to show how the same may be carried into effect, reference will now be made, by way of example, to the accompanying drawings in which like numerals designate corresponding elements or sections throughout.

In the accompanying drawings.

DETAILED DESCRIPTION

Examples of embodiments of the present invention will be explained in more detail by virtue of the following embodiments illustrated in the figures and/or described below.

Figure 1:
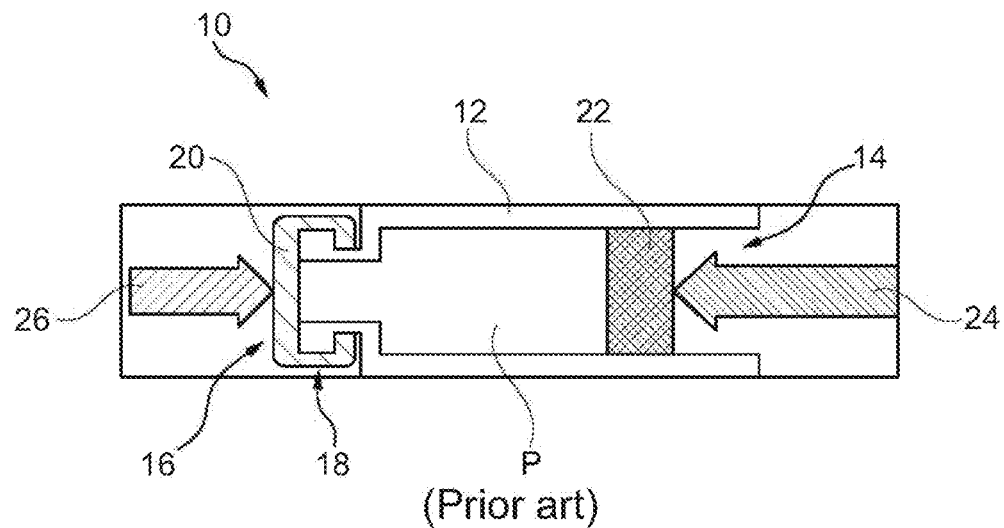
FIG. 1 shows a schematic cross sectional view of a common prior art container assembly.

FIG. 1 shows a container assembly 10 commonly known from the prior art. The container assembly 10 comprises a container 12 having a body portion with an open end 14 and a closed end 16 opposite to the open end 14. In the region of the closed end 16, the body portion comprises a neck portion 18 with a reduced diameter and an adjacent flange portion, wherein the flange portion is closed by a metal crimp 20. The container assembly 10 further comprises a plunger 22 that is slidably arranged inside the body portion via the open end 14.

A pharmaceutical composition P is accommodated in the hollow body portion of the container 12. For expelling or dispensing the pharmaceutical composition P from the container 12, a plunger actuation 24 (relative to the container 12) and a fluidic connection 26 are provided on opposite sides of the container assembly 10. Upon actuation, the plunger actuation 24 acts on the container assembly 10 and causes expelling of the pharmaceutical composition P via the opposite fluidic connection 26. The plunger actuation 24 and the fluidic connection 26 are components of a corresponding medical device (not shown in FIG. 1) and are therefore only schematically illustrated by the arrows 24, 26. The fluidic connection 26 is usually a cannula that before or upon actuation of the medical device pierces through the crimp 20 and a subjacent rubber seal (not shown), which rubber seal is arranged between the crimp 20 and the accommodated pharmaceutical composition P. The container assembly 10 is installable in the corresponding medical device which is therefore designed in accordance with and dependent on the design and configuration of the container assembly 10.

Figure 2:
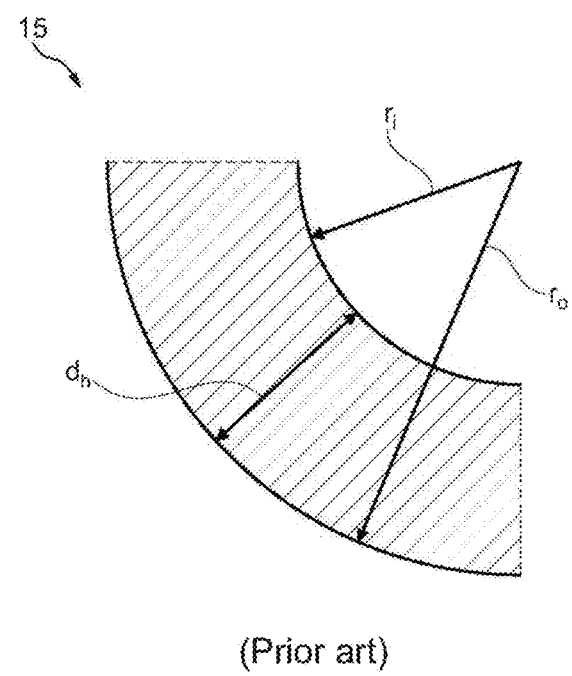
FIG. 2 shows a schematic cross sectional view of a curved heel of a common prior art container.

FIG. 2 shows a cross-sectional view of a curved heel 15 of a common prior art container, which can be a curved glass heel. FIG. 2 illustrates the characterization of such a curved heel 15 by means of the inner radius $r_i$, the outer radius $r_o$ and the thickness of the material $d_h$ in the curved heel 15. In an ordinary glass container of the prior art as shown in FIG. 2, in which a bottom portion (not shown in FIG. 2) has been prepared by simply bending over the heat softened areas of a mother tube and in which no particular measures have been taken to shape the form of the curved heel 15, the circle defined by inner radius $r_i$ and the circle defined by outer radius $r_o$ are located concentric to one another. Under these circumstances, in common prior art containers condition $r_o=r_i+d_h$ is fulfilled. However, according to the present invention the resistance of a container towards axial loads and the burst pressure can be improved if a curved heel is formed deviant from the heel structure of prior art containers.

Figure 3:
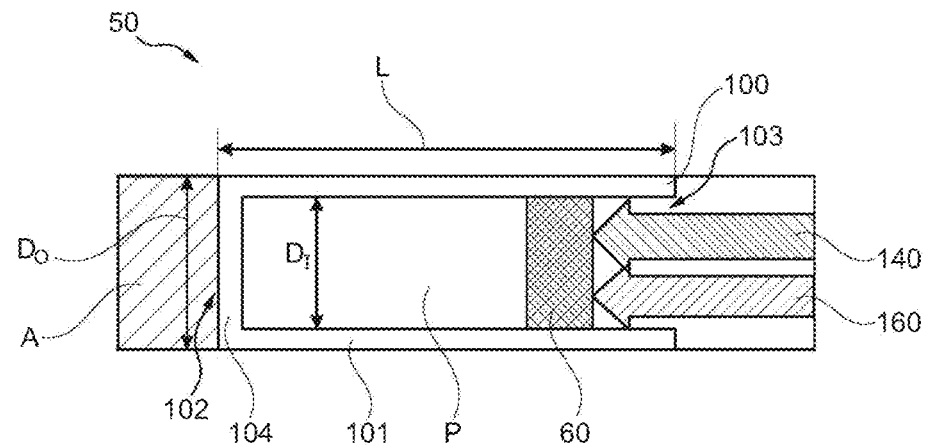
FIG. 3 shows a schematic cross sectional view of a container assembly according to the present invention.

FIG. 3 a schematic cross sectional view of a container assembly 50 according to an exemplary embodiment of the present invention. The container assembly 50 comprises container 100 having a hollow cylindrical body 101 with an open end 103 and a dead end 102 opposite to the open end 103. The cylindrical shape, i.e. the outer diameter $D_o$ and the inner diameter $D_I$, of the hollow cylindrical body 101 is substantially constant over the entire length of the hollow cylindrical body 101 and does not comprise any taper or neck portion. The container assembly 50 further comprises a rubber plunger 60. The rubber plunger 60 is received via the open end 103 in the container 100 and is slidable relative to the hollow cylindrical body 101 from the open end 103 towards the dead end 102.

The dead end 102 is closed by a bottom portion 104 which is formed integrally with and of the same material as the hollow cylindrical body 101, i.e. as the lateral surface (shell surface) of the container 100. In the present example, the container 100, more precisely the hollow cylindrical body 101 and the bottom portion 104 are made of glass, e.g. borosilicate glass. Alternatively, in other embodiments the container 100 can be made of a polymer. The inner surface of the container 100 has an average Zn-leachability of 0.00085 µg/cm² or less.

In the example shown in FIG. 3, the hollow cylindrical body 101 of the container 100 has a length L of 45 mm, an outer diameter $D_o$ of 15 mm and an inner diameter $D_I$ of 12 mm, with a length to outer diameter ratio of 3:1. Alternatively, in other embodiments the container 100 may have a length between 35 mm and 120 mm, preferably between 42 and 70 mm, an outer diameter between 6.85 mm and 30 mm, preferably between 8.65 and 22.05 mm, and/or an inner diameter between 4.65 mm and 27 mm, preferably between 6.85 mm and 19.05 mm, with a length to diameter ratio between 3:1 and 15:1, preferably between 3:1 and 12:1, preferably between 3:1 and 10:1, more preferably between 3:1 and 7:1, more preferably between 4:1 and 7:1, more preferably between 5:1 and 7:1 and more preferably between 6:1 and 7:1.

A pharmaceutical composition P is accommodated in the hollow cylindrical body 101 of the container 100. For expelling or dispensing the pharmaceutical composition P from the container 100, both a plunger actuation 140 (relative to the container 100) and a fluidic connection 160 are realized on the same side of the container 100, i.e. at the open end 103 of the container 100. The plunger actuation 140 and the fluidic connection 160 are components of a corresponding medical device (shown in FIG. 4) and are therefore only schematically illustrated by the arrows 140, 160 in FIG. 3. The fluidic connection 160 can be a cannula that upon actuation of the medical device pierces through the rubber plunger 60. Further, upon and during actuation, the container 100 is moved axially relative to the plunger 60 and the fluidic connection 160.

By providing the container 100 with a dead end 102 in contrast to the prior art crimp assembly, the neck portion, the flange, the rubber seal and the crimp can be omitted. Thus, the container 100 comprises less components than the prior art assembly and has a more compact size and shape. The dashed area A shown in FIG. 3 represents the overall volume reduction in a corresponding medical device that can be gained by the container 100 according to the present invention compared to the prior art crimp-type container.

Figure 4:
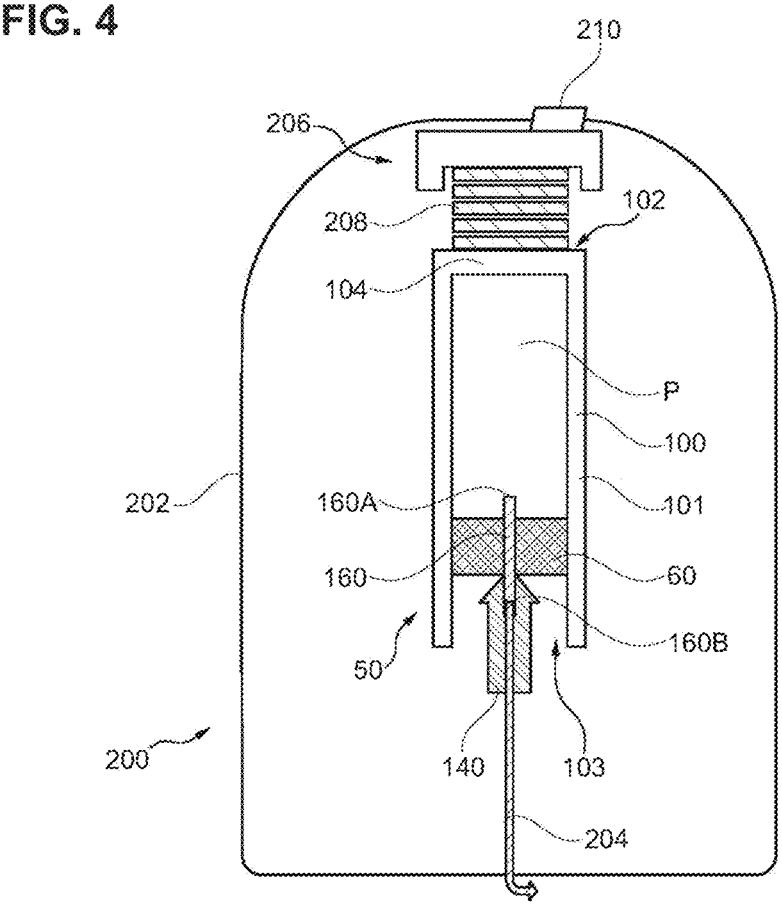
FIG. 4 shows a schematic cross sectional view of a medical device according to the present invention comprising the container assembly of FIG. 2.

The container assembly 50 is installable in a medical device. A medical device 200 according to an exemplary embodiment of the present invention is schematically shown in FIG. 4. The medical device 200 comprises a hollow device body 202 (a device housing), in which the container assembly 50 and further components of the medical device 200 are housed. Same reference signs are used throughout the figures for the same or mutually corresponding elements and features.

As shown in FIG. 4 the fluidic connection 160 is a cannula that pierces through the plunger 60 and extends with a first end 160A into the hollow cylindrical body 101 of the container 100. An opposite second end of the cannula 160 is fluidically connected to a tube 204 for expelling the pharmaceutical composition P accommodated in the container 100 via the cannula 160 and the tube 204. The tube 204 can be fluidically connected to further components of the medical device 200 or a connected device.

In the example of FIG. 4, the plunger actuation 140 relative to the container 100, more precisely the movement of the container 100 relative to the plunger 60 is realized by the actuation mechanism 206. The actuation mechanism 206 comprises a spring 208, which in an initial position (unactuated state) is preloaded. The actuation mechanism 206 further comprises a trigger 210. Upon actuation of the medical device 200 by operating the trigger 210, the spring 208 applies force to and thus moves the container 100 relative to the plunger 60 and relative to the cannula 160. The plunger 60 and the cannula 160 maintain stationary during actuation and use of the medical device 200. By moving the container 100 relative to the stationary plunger 60, the plunger 60 applies pressure to the accommodated pharmaceutical composition P, which is thus expelled via the cannula 160 and the fluidically connected tube 204.

Figure 5:
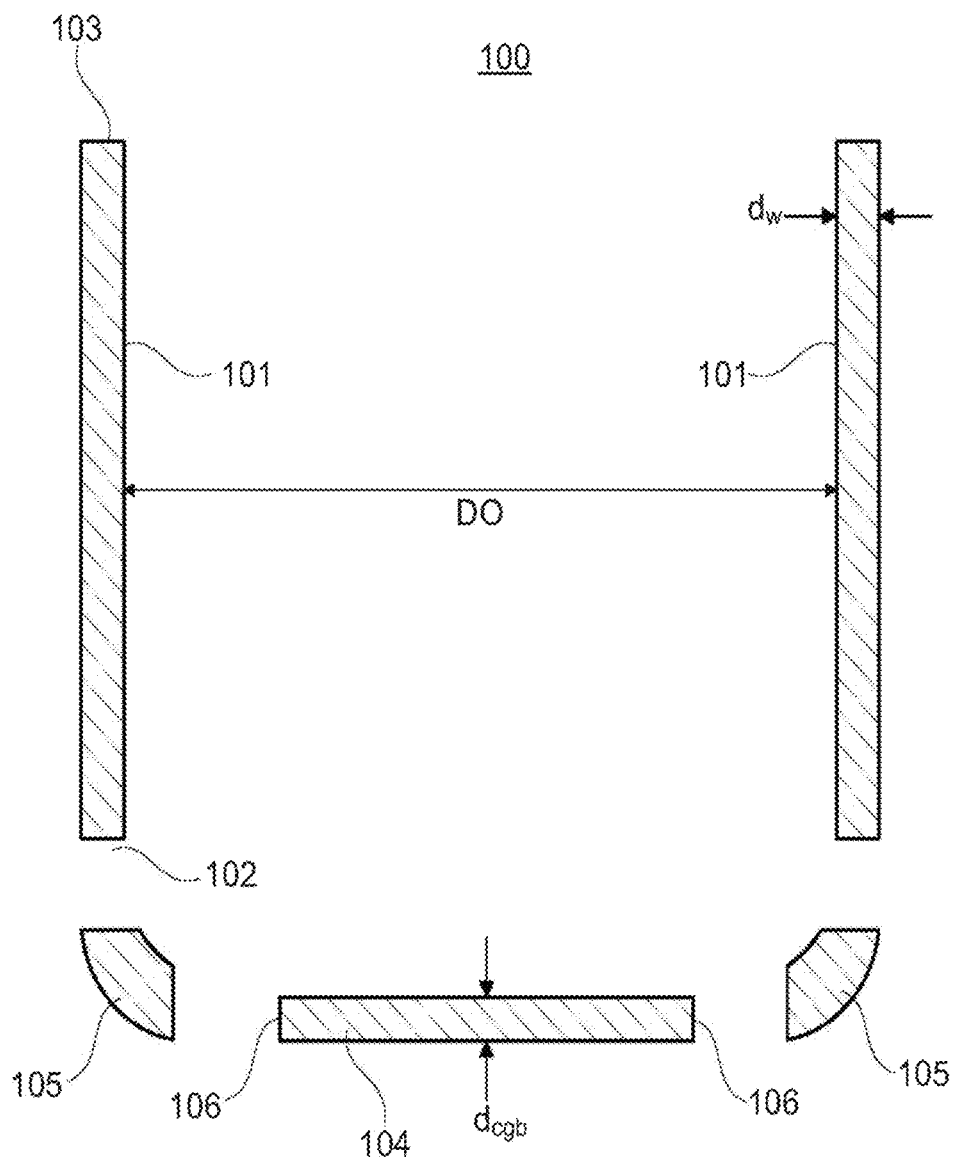
FIG. 5 shows a cross sectional view of a container according to the invention, wherein for the purpose of an improved illustration the parts of the container have been separated from each other.

FIG. 5 shows a cross-sectional view of the container 100 according to the invention. In the shown example, the container 100 is a glass container. For the purpose of an improved illustration the individual parts of the container 100 (i. e. the hollow cylindrical body 101, the bottom portion 104 and the curved heel 105) have been illustrated separate from each other, even though these components are formed integrally. However, as the container 100 according to the invention is preferably obtained by a process in which a mother tube (which forms the hollow cylindrical body 101), while rotating around its major axis, is heated to its softening point with flames, in which the heated glass is pulled along its major axis for stretching and creating a container dead end and in which the container dead end has been shaped to form a bottom portion 104 and a curved heel 105, these parts are integrally connected in the container 100 according to the present invention. As shown in FIG. 5, the hollow cylindrical body 101 is characterized by the dead end 102 and the opposite open end 103. The bottom portion 104 comprises an outer region 106 that in the container 100 is connected to the curved heel 105. The bottom portion 104 is characterized by a thickness in the centre $d_{cgb}$ of the bottom portion 104, whereas the hollow cylindrical body 101 is characterized by a wall thickness $d_w$.

Figure 6A:
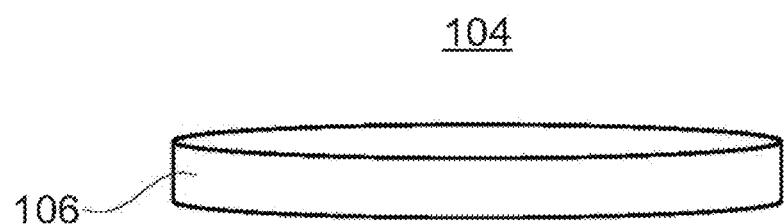
FIG. 6A shows a schematic depiction of the bottom portion of the container.
Figure 6B:
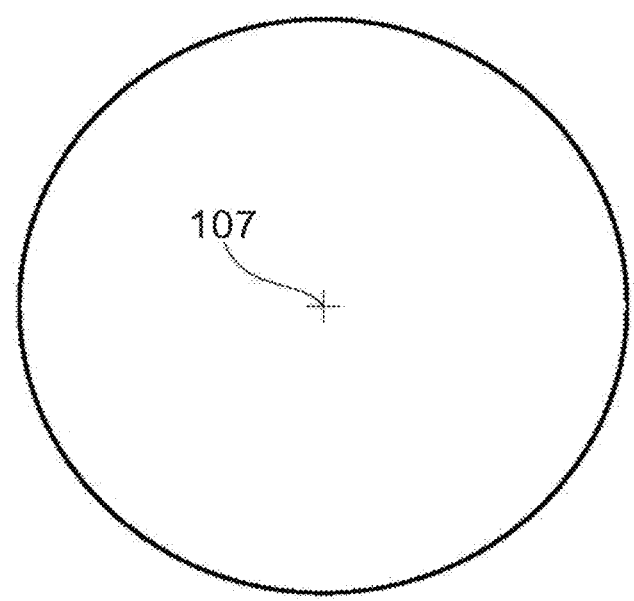
FIG. 6B shows a top view of the bottom portion of the container.
Figure 6C:
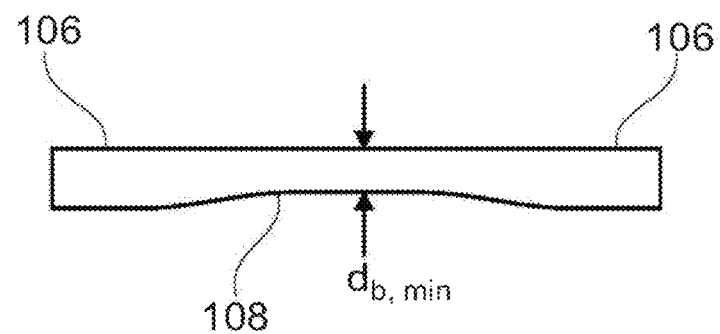
FIG. 6C shows a cross sectional view of the bottom portion of the container.

FIG. 6 shows the bottom portion 104 from different perspectives, wherein in the shown example the bottom portion 104 is a circular glass bottom. FIG. 6A shows a schematic depiction of the bottom portion 104 and the outer region 106 of the bottom portion that in the container 100 according to the invention merges into the curved glass heel 105 (which then merges into the dead end 102 of the hollow cylindrical body 101). FIG. 6B shows a top view of the bottom portion 104 with the centre 107. FIG. 6C shows a cross-sectional view of the circular bottom portion 104. As shown in this figure, the thickness of the material in the bottom portion 104 can vary with the area from the centre 107 towards the outer region 106. In the bottom portion 104 shown in FIG. 6C the thickness reaches its lowest point $d_{b,min}$ at the centre 107 of the bottom portion 104. As a consequence of the above described nature of the process of forming a bottom portion 104 and the curved heel 105 from a mother tube 101 the exterior surface of the bottom portion is not necessarily flat, but often has a concave indentation 108 as shown in FIG. 6C.

Figure 7:
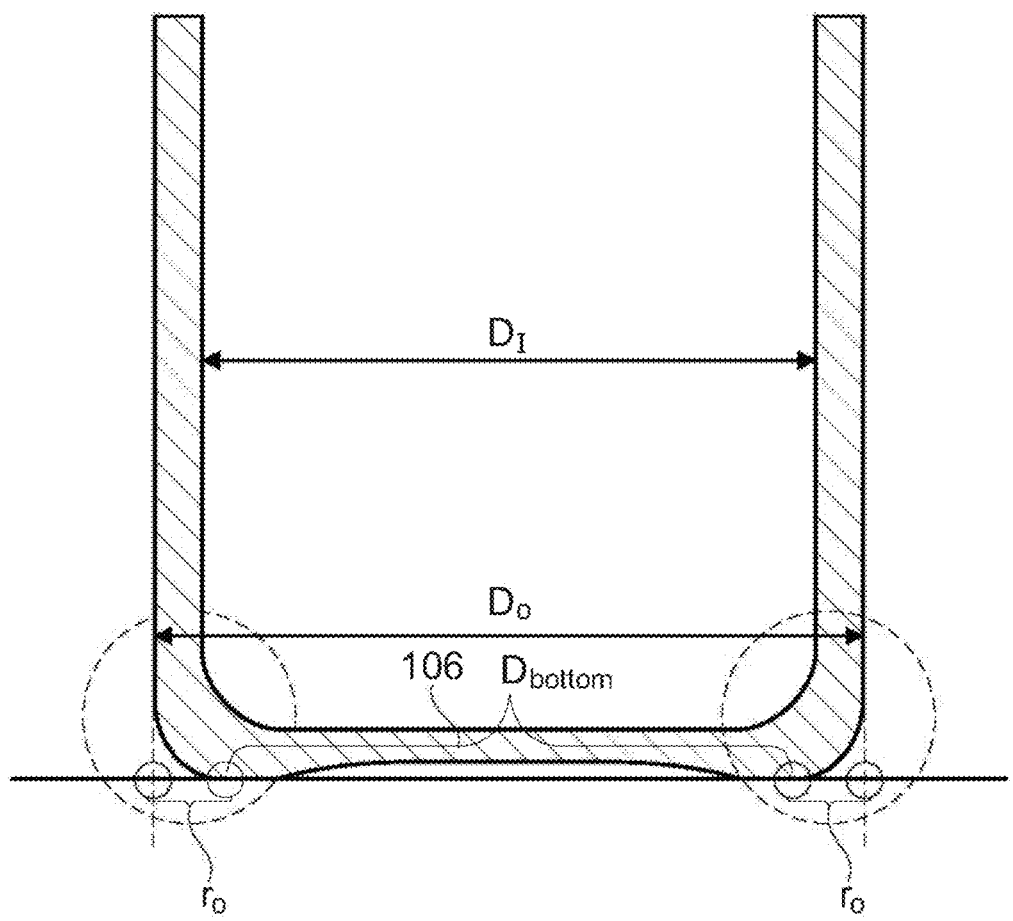
FIG. 7 shows a cross sectional view of a further container according to the invention.

FIG. 7 shows a cross sectional view of the container 100. The hollow cylindrical body 101 of the container 100 has an inner diameter $D_I$ and an outer diameter $D_o$, wherein $D_o > D_I$. The dotted circles at the bottom show the curved heel 105 of the container 100. The section covered by the dotted circles is shown in an enlarged view in FIG. 8. The circular bottom portion 104 is characterized by a bottom diameter $D_{bottom}$, wherein $D_{bottom} = D_O - 2 \times r_o$ ($D_O$ corresponds to the outer diameter of the hollow cylindrical body 101 and $r_o$ is the outer radius of the curved heel 105 measured by means of the approach shown in FIG. 12A).

Figure 8:
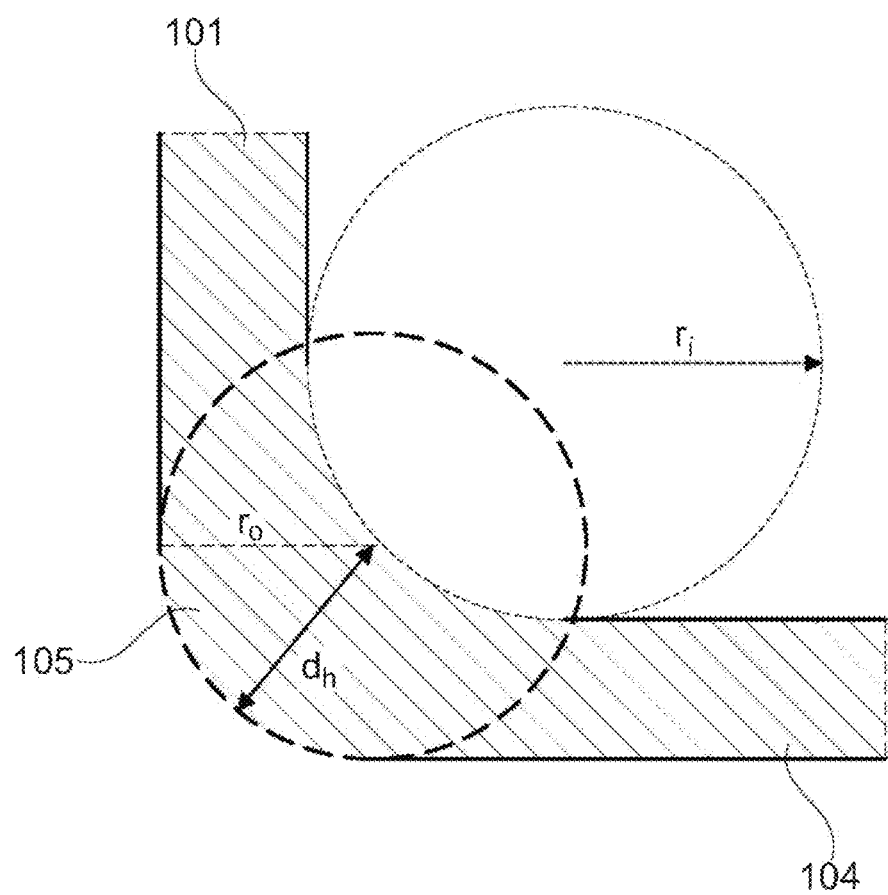
FIG. 8 shows an enlarged cross sectional view of the curved heel of a container according to the invention.

FIG. 8 shows an enlarged view of the curved heel 105 of container 100 according to the invention, in which the inner and outer contour of the heel 105 are substantially arc-shaped. As can be seen, the structure of the curved heel 105 deviates from the structure of the heel in prior art containers as shown in FIG. 2. In the configuration of the embodiment according to the invention, the thickness $d_h$ of the material in the area of the curved heel 105 has been increased and the outer radius $r_o$ has been reduced to ensure that a certain minimum value for the term $d_h^3/(r_o \times d_w)$ is reached. Furthermore, the inner radius $r_i$ also has been increased.

Figure 9:
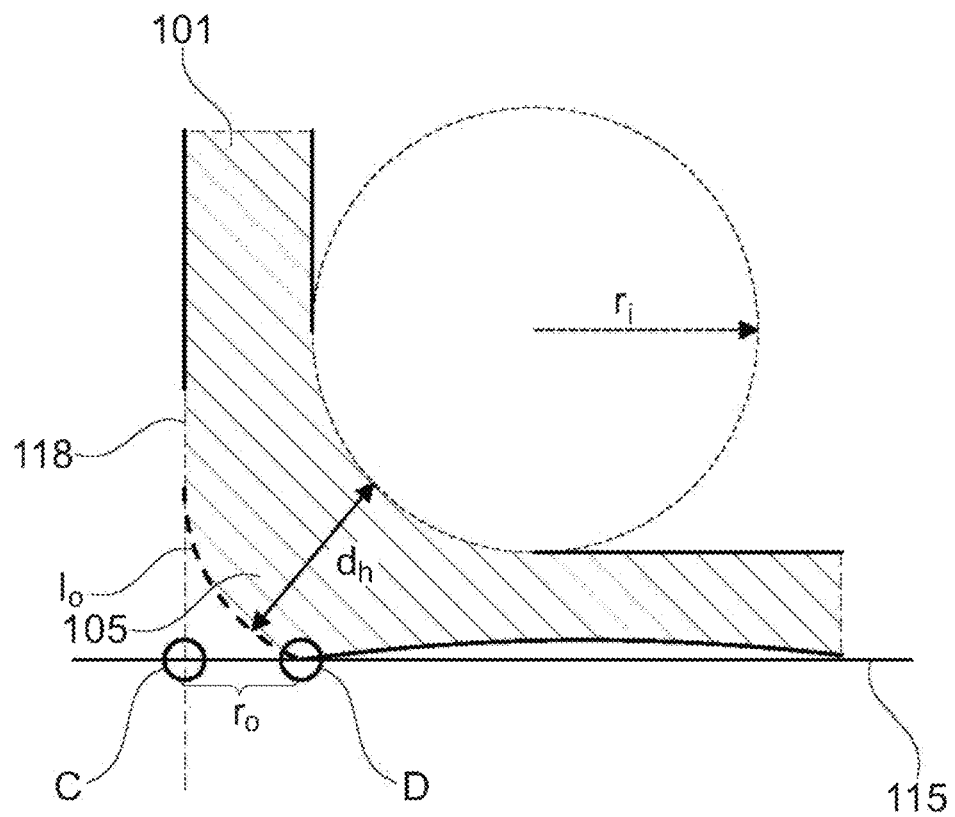
FIG. 9 shows an enlarged cross sectional view of a further embodiment of the curved heel of a container according to the invention.

FIG. 9 shows an enlarged view of a further curved heel 105 in a container 100 embodiment according to the invention, in which the inner and outer contour of the heel 105 are substantially arc-shaped, but in which—contrary to the curved heel shown in FIG. 8—the length of the circular arc at the outer surface of the curved heel is smaller than $2 \times \pi \times r_o/4$. In this case $r_o$ does not correspond to the outer radius of the curved heel, but to width of the material overhang in the area of the curved heel that is defined by the distance between points "C" and "D" (for the determination of $r_o$ see again FIG. 12A).

Figure 10A:
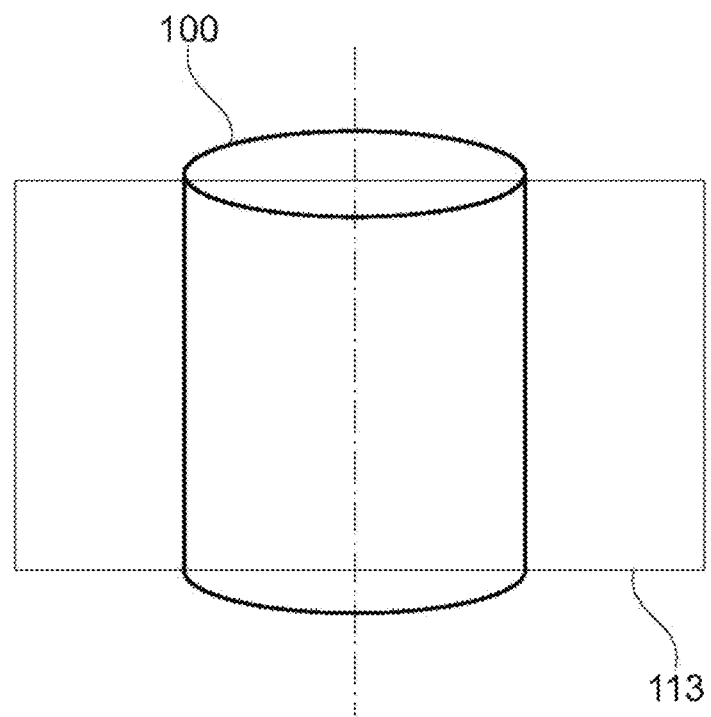
FIG. 10A shows in a side view the localization of plane that is used to determine $r_o$, $r_i$, and $d_h$ by means of the approaches that are shown in FIGS. 11A, 11B, 11C, 12A and 12B.
Figure 10B:
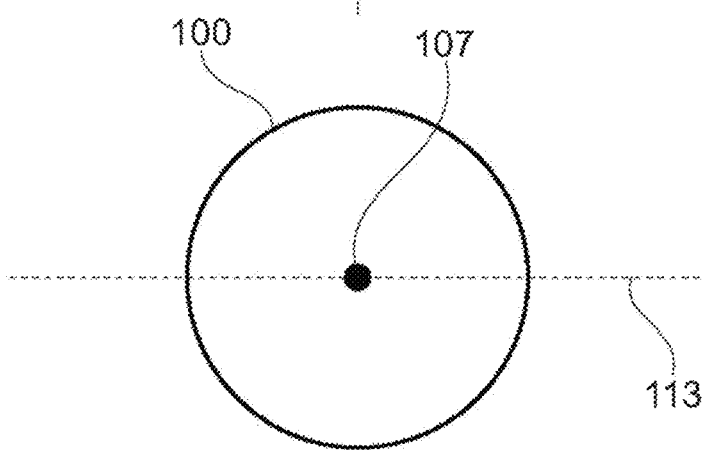
FIG. 10B shows in a top view the localization of plane that is used to determine $r_o$, $r_i$ and $d_h$ by means of the approaches that are shown in FIGS. 11A, 11B, 11C, 12A and 12B.

FIGS. 10A and 10B show in a side view and in a top view the localization of plane 113 in the container 100 that is used to determined $r_o$, $r_i$ and $d_h$ by means of the approaches that are shown in FIGS. 11A, 11B, 11C, 12A and 12B. Plane 113 corresponds to the plane that is centrically located in the container 100 and that comprises the longitudinal axis of the container (indicated by the dashed line in FIG. 10A), i. e. the axis that goes perpendicular through the centre 107 of the bottom (see FIG. 10B).

Figure 11A:
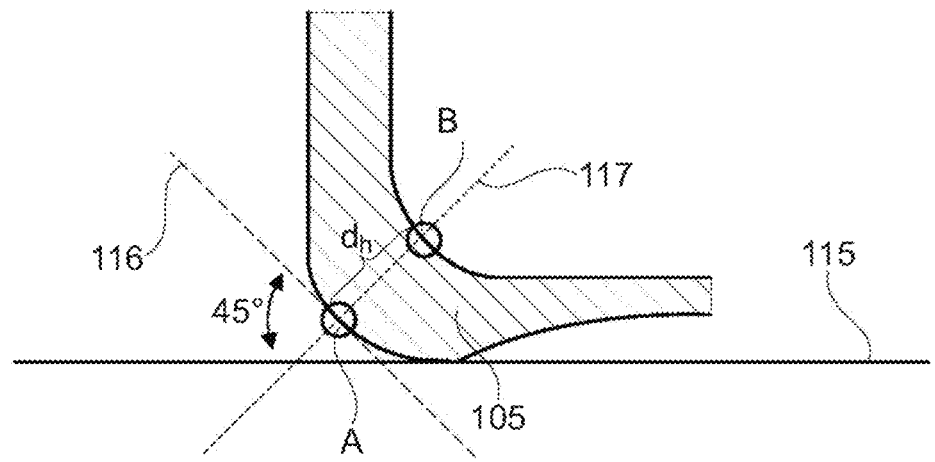
FIG. 11A illustrates the determination of $d_h$ in a curved heel.

FIG. 11A illustrates the determination of $d_h$ in a curved heel 105 in plane 113. For the determination of $d_h$ a tangent 116 that confines an angle of 45° with the ground-level bearing surface 115 is placed at the exterior surface of the curved heel 105. The point of the exterior surface of the curved heel 105 that comes into contact with the 45-tangent 116 is designated as "A" (see the lower circle in FIG. 11A). Next, a straight line 117 orthogonal to 45°-tangent 116 is guided through point "A". The position at which this straight orthogonal line 117 breaks through the interior side of the curved heel 105 is designated as "B" (see the upper circle FIG. 11A). $d_h$ corresponds to the distance between points "A" and "B".

Figure 11B:
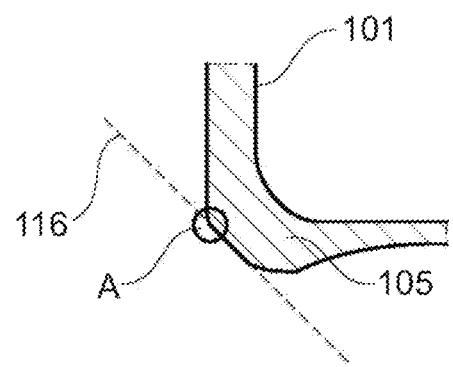
FIGS. 11B-11C show different shapes of the exterior surface of a curved heel.
Figure 11C:
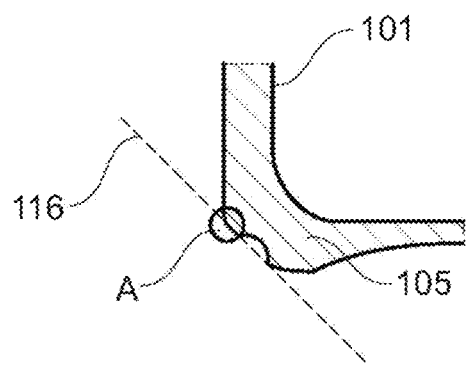

FIGS. 11B-11C show curved heels 105 having a shape such that there are more than only one point of exterior surface of the curved heel 105 that comes into contact with the 45-tangent 116. In such a case point "A" corresponds to the point that is nearest to the outer surface of hollow cylindrical body 101 of the container 100.

Figure 12A:
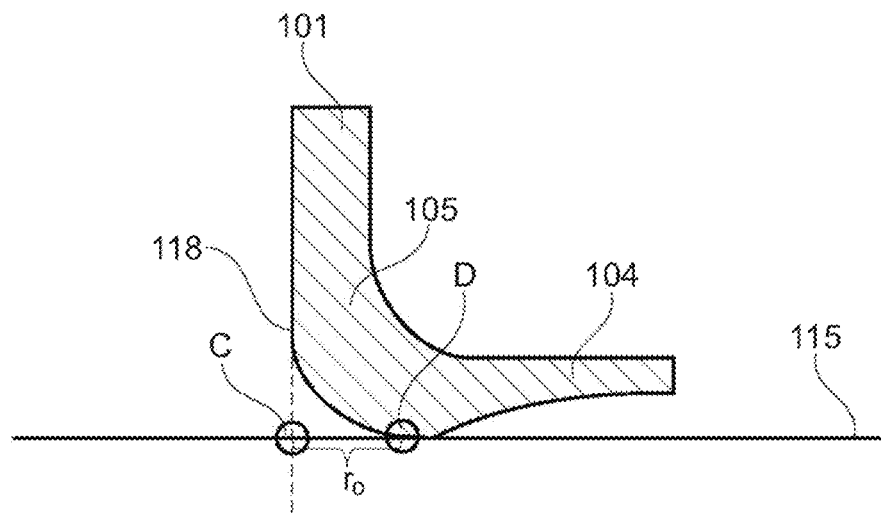
FIG. 12A illustrates the determination of $r_o$ in a curved heel.

FIG. 12A illustrates the determination of $r_o$ in a curved heel 105 in plane 113. For the determination of $r_o$ the intersection point of a first straight line 118 that forms an elongation of the exterior side of the hollow cylindrical body 101 and the ground-level bearing surface 115 is determined. This intersection point is designated as "C" (see the left circle in FIG. 12A). Next, the point of the exterior surface of the container 100 that contacts the ground-level bearing surface 115 and that is closest to point "C" is determined. This intersection point is designated as "D" (see the right circle in FIG. 12A). $r_o$ corresponds to the distance between points "C" and "D".

Figure 12B:
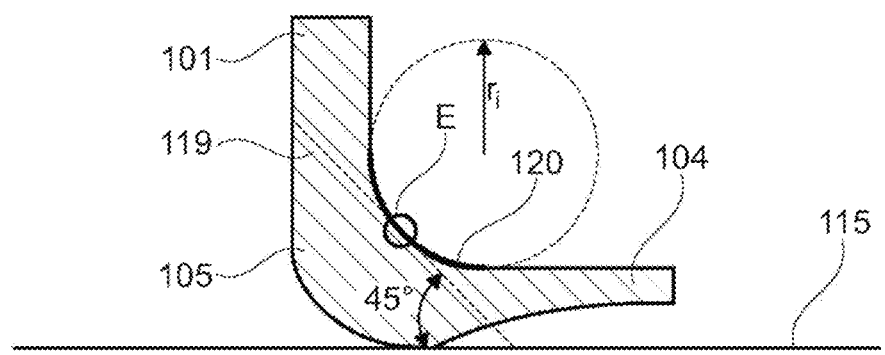
FIG. 12B illustrates the determination of $r_i$ in a curved heel.

FIG. 12B illustrates the determination of $r_i$ in a curved heel 105 in plane 113. For the determination of $r_i$ a tangent 119 that confines and angle of 45° with the ground-level bearing surface 115 is placed at the interior surface of the curved heel 105. The point of the interior surface of the curved heel 105 that comes into contact with the 45-tangent 119 is designated as "E" (see the small circle in FIG. 12B). Next, the largest quarter circle 120 is determined that can be properly positioned on the inner contour of the curved heel 105, that comprises point "E" in the middle of the quarter circle and the ends of which do not extend into the mass of glass. $r_i$ corresponds to the radius of the largest quarter circle 120

If there are more than only one point of interior surface of the curved heel 105 that comes into contact with the 45°-tangent 119, point "E" corresponds to the geometric centre between points "P1" and "P2", wherein point "P1" is the point on the 45°-tangent 119 that comes into contact with the interior surface of the curved heel and that is located nearest to the hollow cylindrical body 101 and point "P2" is the point on the 45°-tangent 119 that comes into contact with the interior surface of the curved heel 105 and that is located nearest to the bottom portion 104.

Figure 13A:
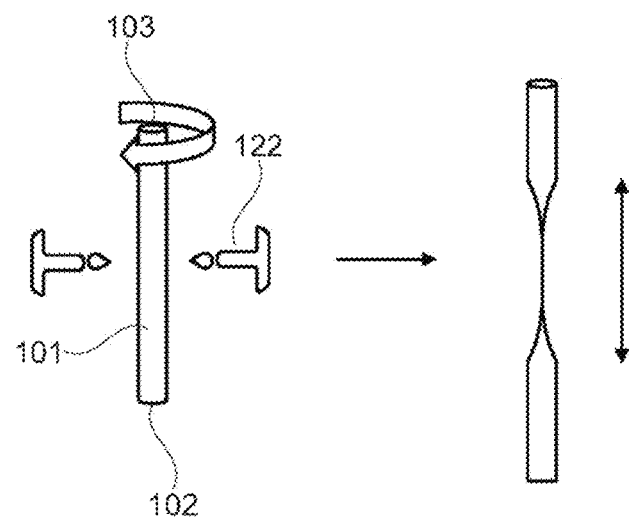
FIG. 13A illustrates steps I), II) and III) of a process for the preparation of a glass container according to the invention.
Figure 13B:
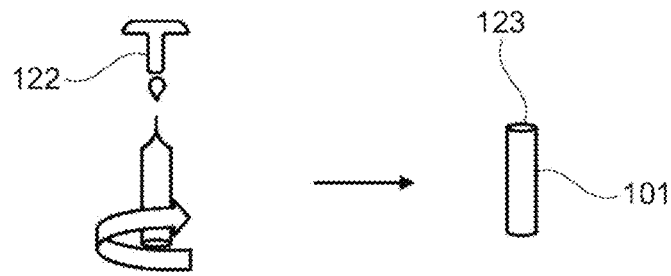
FIG. 13B illustrates step IV) of the process for the preparation of a glass container according to the invention.

FIG. 13 illustrates a first process for the preparation of a glass container 100 according to the invention. FIG. 13A illustrates process steps I), II) and III), wherein in process step I) a glass tube 101 with a first 102 and a further end 103 is provided, the glass tube having a wall thickness of $d_w$ (not shown in FIG. 13A). In process step II), the glass tube is heated, while rotating around its major axis, to its softening point with a heating element (indicated by the candle flames shown on the left in FIG. 13A), preferably with a flame 122. In process step III) the heated glass tube is pulled along its major axis for stretching as shown on the right in FIG. 13A, thereby creating a container closure 123. In process step IV), depicted in FIG. 13B, container closure 123 is shaped to form a glass bottom portion 104 and a curved glass heel 105 (not shown in FIG. 13B) via which the glass bottom portion 104 is connected to the glass tube/the hollow cylindrical body portion 101.

Figure 14A:
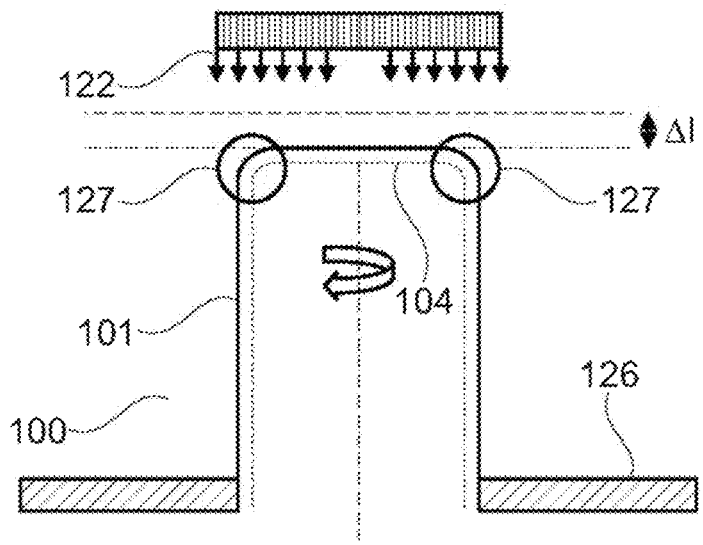
FIG. 14A illustrates a sub-step in the formation of the shape of the curved heel according to the present invention.

FIG. 14A illustrates a sub-step in the formation of the desired shape of the curved glass heel 105 in glass container 100 according to the present invention. For the formation of the desired shape of the curved glass heel 105 a glass container 100 that is fixed in an fixing element 126 of a rotary machine and that is continuously rotated around its longitudinal axis as shown in FIG. 14A is brought in an upward position with the glass bottom showing to the top. In a first sub-step, the glass bottom is heated with a burner 122 in which the peripheral zone (as indicated by the arrows at the top of FIG. 14A) is heated to a larger extend compared to the middle section so that the area in the peripheral zone of the glass bottom 104 (i.e. in an area indicated by the circles in FIG. 14A that comprises the curved glass heel and the part of the hollow cylindrical body 101 that is in contact with the curved glass heel 105) are particularly heated. As a result, a melting of the bottom portion 104 even into the wall of the hitherto hollow cylindrical body 101 occurs so that the glass contracts slightly under the surface tension and the bottom slightly sinks (see Δl in FIG. 14A). This leads to an increased accumulation of glass in the peripheral zone 127 of the bottom portion 104 (indicated by the circles in FIG. 14A), compared to a prior art process in which the surface of the glass floor is heated evenly and only to such a degree as necessary to enable bottom forming. The additional mass of glass in the peripheral zone 127 of the glass bottom 104 thus arises from the hitherto cylindrical wall of the hollow cylindrical body 101 which is adjacent to the curved heel 105.

Figure 14B:
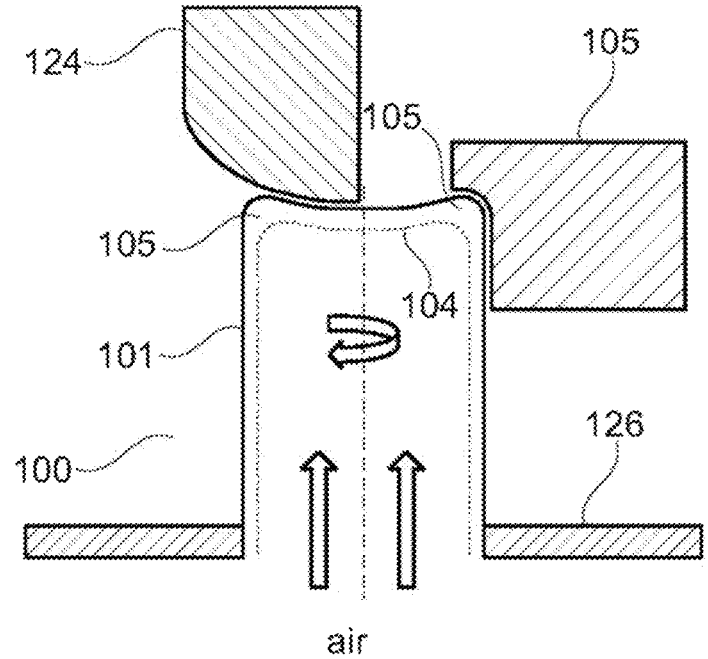
FIG. 14B illustrates a further sub-step in the formation of the shape of the curved heel according to the present invention.

FIG. 14B illustrates a further sub-step in the formation of the shape of the curved glass heel 105 in the glass container 100 according to the present invention. In this sub-step the glass container 100 is still continuously rotated around its longitudinal axis and the glass bottom 101 is concavely pushed inward by a die 124, while at the same time an air flow from below pushes the bottom portion 104 of the container 100 against the die 124 so that it does not sink under gravity. At the same time a molding roller 125 is provided which predetermines the outer shape of the curved glass heel 105 and which prevents the glass mass accumulated in the peripheral zone 127 from escaping to the outside. Simultaneously, the air flow and the die 124 cause the bottom portion 104 and the peripheral zone 127 to cool down quickly until it these areas are no longer shapeable.

Figure 15:
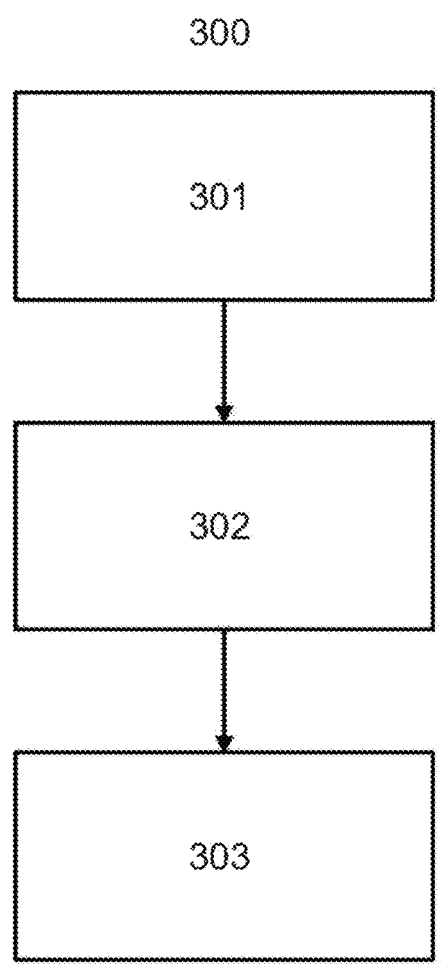
FIG. 15 shows a flow chart of another process for packaging a pharmaceutical composition in a container assembly according to the invention.

FIG. 15 shows a flow chart of a process 300 for packaging a pharmaceutical composition. In a process step a) 301, the container 100 according to one of the embodiments of the invention is provided. In a process step b) 302, a pharmaceutical composition is filled into the interior volume $V_i$ of the container 100, and in a process step c) 303 the open end 103 of the container 100 is closed by a plunger 60.

LIST OF REFERENCE SIGNS

| | | | |
|---|---|---|---|
| P | pharmaceutical composition | L | length |
| 50 | container assembly | $D_O$ | outer diameter |
| 60 | plunger | $D_I$ | inner diameter |
| 100 | container | $D_{bottom}$ | bottom diameter |
| 101 | hollow cylindrical body | $r_O$ | outer radius of curved heel |
| 102 | dead end | | |
| 103 | open end | $r_I$ | inner radius of curved heel |
| 104 | bottom portion | | |
| 105 | curved heel | $d_W$ | wall thickness |
| 106 | outer region of the bottom portion | $d_h$ | thickness in the center of curved heel |
| 107 | center of the bottom portion | | |
| 108 | concave indentation | $l_O$ | length of circular arc |
| 113 | plane | $d_{cgb}$ | thickness at center of the bottom |
| 115 | ground-level bearing surface | | |
| 116 | 45°-tangent at the exterior surface of the curved heel | $d_{b,\ min}$ | minimum thickness of the bottom |
| | | 200 | medical device |
| 117 | straight line orthogonal to 45°-tangent | 202 | hollow device body (device housing) |
| 118 | straight line forming an elongation of the hollow cylindrical body | 204 | tube |
| | | 206 | actuation mechanism |
| 119 | 45°-tangent at the interior surface of the curved heel | 208 | spring |
| | | 210 | trigger |
| 120 | largest quarter circle | 300 | process |
| 122 | heating element, preferably a flame | 301 | process step a) |
| 123 | container closure | 302 | process step b) |
| 124 | die | 303 | process step c) |
| 125 | molding roller | 10 | container assembly (prior art) |

-continued

LIST OF REFERENCE SIGNS

| | | | |
|---|---|---|---|
| 126 | fixing element of a rotary machine | 12 | container (prior art) |
| 127 | peripheral zone of the bottom in which material accumulates | 14 | open end (prior art) |
| 140 | plunger actuation | 14 | curved heel (prior art) |
| 160 | fluidic connection (cannula) | 16 | closed end (prior art) |
| 160A | first end of the cannula | 18 | neck portion (prior art) |
| 160B | second end of the cannula | 20 | crimp (prior art) |
| A | overall volume reduction | 22 | plunger (prior art) |
| | | 24 | plunger actuation (prior art) |
| | | 26 | fluidic connection (prior art) |

What is claimed is:

1. A container for accommodating pharmaceutical compositions, the container comprising:
   a hollow cylindrical body having an open end and a dead end opposite to the open end,
   the open end being configured to receive a plunger that is slidable relative to the hollow cylindrical body from the open end towards the dead end;
   a bottom portion closing the dead end, the hollow cylindrical body and the bottom portion being formed integrally and of a common material, the common material comprises glass or polymer;
   a curved heel between the bottom portion and the hollow cylindrical body,
   wherein the curved heel is defined by an outer radius ($r_o$) in mm, an inner radius ($r_i$) in mm, and a thickness ($d_h$) in mm in a center portion of the curved heel, and
   wherein the curved heel fulfills: $r_i + d_h - r_o > 0.1$ mm; and
   a burst pressure of at least 110% compared to a comparative container which only differs from the container in that the comparative container does not fulfill $r_i + d_h - r_o > 0$ mm.

2. The container of claim 1, wherein the hollow cylindrical body has a length (L) in mm, an outer diameter ($D_o$) in mm, an inner diameter ($D_I$) in mm, a difference (D) between the outer diameter ($D_o$) and the inner diameter ($D_I$) in mm,
   wherein the common material has a tensile strength (Ts) in MPa, and
   wherein $1.00$ MPa $\leq A \leq 12.00$ MPa, where $A = D \times Ts \div L$.

3. The container of claim 1, wherein the hollow cylindrical body has a length (L) in mm, an outer diameter ($D_o$) in mm, an inner diameter ($D_I$) in mm, a difference (D) between the outer diameter ($D_o$) and the inner diameter ($D_I$) in mm,
   wherein the common material has a Young's modulus (E) in GPa, and
   wherein $0.10$ GPa $\leq B \leq 10.00$ GPa, where $B = D \times E \div L$.

4. The container of claim 1, further comprising a pressure compliance of at least 0.64 N/mm²×(inner diameter)².

5. The container of claim 1, wherein the hollow cylindrical body has a wall thickness ($d_w$) in mm, a length (L) between 35 mm and 120 mm, an outer diameter ($D_o$) between 8.65 mm and 30 mm, an inner diameter ($D_I$) between 4.65 mm and 27 mm, and a ratio of the length (L) to the outer diameter ($D_o$) of between 3:1 and 15:1.

6. The container of claim 1, wherein the hollow cylindrical body has an outer diameter ($D_o$) in mm, an inner diameter ($D_I$) in mm, and a length (L) in mm, wherein the outer diameter ($D_o$) and/or the inner diameter ($D_I$) varies not more than 5% over the length (L).

7. A container for accommodating pharmaceutical compositions, the container comprising:
   a hollow cylindrical body having an open end and a dead end opposite to the open end,
   the open end being configured to receive a plunger that is slidable relative to the hollow cylindrical body from the open end towards the dead end;
   a bottom portion closing the dead end, the hollow cylindrical body and the bottom portion being formed integrally and of a common material, the common material comprises glass or polymer;
   a curved heel between the bottom portion and the hollow cylindrical body,
   wherein the curved heel is defined by an outer radius ($r_o$) in mm, an inner radius ($r_i$) in mm, and a thickness ($d_h$) in mm in a center portion of the curved heel, and
   wherein the curved heel fulfills: $r_i + d_h - r_o > 0.1$ mm; and
   a vertical load strength of at least 110% compared to a comparative container which only differs from the container in that the comparative container does not fulfill $r_i + d_h - r_o > 0$ mm.

8. The container of claim 1, wherein the hollow cylindrical body has a wall thickness ($d_w$) in mm, and wherein one or more of the following conditions is/are fulfilled:
   $d_h^3 \pm (r_o \times d_w) > 0.8$ mm,
   $[(100 \times d_h^3 \times r_i) \div (d_w \times D_o^2)] + (4.4 \text{ mm}^2 \div D_o) > 0.55$ mm, and
   $r_i > 0.7$ mm.

9. The container of claim 1, wherein the bottom portion is a circular bottom having a minimum thickness ($d_{b,min}$), and wherein $d_h \div d_{b,min} < 3.0$.

10. The container of claim 1, wherein the common material is cycloolefin copolymer or cycloolefin polymer.

11. The container of claim 1, further comprising an inner surface having an average Zn-leachability of 0.00085 µg/cm² or less.

12. The container of claim 1, further comprising an inner surface having an average Zn-leachability of 0.00055 µg/mm² or less.

13. A container assembly for accommodating pharmaceutical compositions, the container assembly comprising:
   a plunger configured to be pierceable by a cannula;
   a hollow cylindrical body having an open end and a dead end opposite to the open end,
   the open end receiving the plunger at the open end so as to sealingly close the open end, the plunger being slidable relative to the hollow cylindrical body from the open end towards the dead end;
   a bottom portion closing the dead end, the hollow cylindrical body and the bottom portion being formed integrally and of a common material, the common material comprises glass or polymer;
   a curved heel between the bottom portion and the hollow cylindrical body,
   wherein the curved heel is defined by an outer radius ($r_o$) in mm, an inner radius ($r_1$) in mm, and a thickness ($d_h$) in mm in a center portion of the curved heel, and wherein the curved heel fulfills: $r_i+d_h-r_o>0.1$ mm; and a burst pressure of at least 110% compared to a comparative container which only differs from the container in that the comparative container does not fulfill $r_i+d_h-r_o>0$ mm.

14. A container assembly for accommodating pharmaceutical compositions, the container assembly comprising:
   a plunger configured to be pierceable by a cannula;
   a hollow cylindrical body having an open end and a dead end opposite to the open end,
the open end receiving the plunger at the open end so as to sealingly close the open end, the plunger being slidable relative to the hollow cylindrical body from the open end towards the dead end;
   a bottom portion closing the dead end, the hollow cylindrical body and the bottom portion being formed integrally and of a common material, the common material comprises glass or polymer;
   a curved heel between the bottom portion and the hollow cylindrical body,
   wherein the curved heel is defined by an outer radius ($r_o$) in mm, an inner radius ($r_i$) in mm, and a thickness ($d_h$) in mm in a center portion of the curved heel, and
   wherein the curved heel fulfills: $r_i+d_h-r_o>0.1$ mm; and
   a vertical load strength of at least 110% compared to a comparative container which only differs from the container in that the comparative container does not fulfill $r_i+d_h-r_o>0$ mm.

15. The container assembly of claim 13, wherein the hollow cylindrical body has a length (L) in mm, an outer diameter ($D_o$) in mm, an inner diameter ($D_I$) in mm, a difference (D) between the outer diameter ($D_o$) and the inner diameter ($D_I$) in mm,
   wherein the common material has a tensile strength (Ts) in MPa and a Young's modulus (E) in GPa,
   wherein 1.00 MPa≤A≤12.00 MPa, where A=D×Ts÷L, and/or
   wherein 0.10 GPa.≤B≤10.00 GPa, where B=D×E÷L.

16. The container assembly of claim 13, further comprising a pharmaceutical composition in the hollow cylindrical body.

17. A medical device for expelling or injecting pharmaceutical compositions, comprising:
   the container assembly of claim 16;
   a cannula for expelling the pharmaceutical composition from the container assembly through the cannula, wherein the cannula is arranged so as to pierce the plunger upon actuation, and
   an actuation mechanism configured to move the container and the plunger relative to each other in a substantially axial direction to apply pressure to the pharmaceutical composition accommodated in the container for expelling the pharmaceutical composition through the cannula.

* * * * *